US 8,337,705 B2

(12) United States Patent
Vogeser

(10) Patent No.: US 8,337,705 B2
(45) Date of Patent: *Dec. 25, 2012

(54) MANIPULATION OF MAGNETIC MICROPARTICLES IN A HIGH PRESSURE LIQUID SYSTEM AND EXTRACTION PROCESS

(75) Inventor: Michael Vogeser, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/464,153

(22) Filed: May 12, 2009

(65) Prior Publication Data

US 2010/0326909 A1 Dec. 30, 2010

Related U.S. Application Data

(63) Continuation-in-part of application No. 12/328,228, filed on Dec. 4, 2008.

(30) Foreign Application Priority Data

Dec. 8, 2008 (EP) ..................................... 08021311

(51) Int. Cl.
*B03C 1/02* (2006.01)
*G01N 1/34* (2006.01)
*G01N 21/00* (2006.01)

(52) U.S. Cl. ..... 210/695; 210/635; 210/806; 210/198.2; 210/257.1; 210/259; 210/295; 422/68.1; 422/70; 422/82.05; 422/82.08; 422/527; 436/526

(58) Field of Classification Search .................. 436/526; 422/68.1, 70, 82.05, 82.08, 527; 210/635, 210/695, 806, 198.2, 257.1, 259, 295

See application file for complete search history.

(56) References Cited

U.S. PATENT DOCUMENTS 7,033,473 B2 * 4/2006 Gascoyne et al. ............ 204/547
(Continued)

FOREIGN PATENT DOCUMENTS

EP 0905520 A1 3/1999
(Continued)

OTHER PUBLICATIONS

EPO Search Report dated Feb. 11, 2001 for EP Application No. EP 08 02 1311.
Hubbuch et al., "High-Gradient Magnetic Affinity Separation of Trypsin from Porcine Pancreatin," Biotechnology and Bioengineering, vol. 79, No. 3, Aug. 5, 2002, pp. 301-313.
(Continued)

*Primary Examiner* — David A Reifsnyder
(74) *Attorney, Agent, or Firm* — Roche Diagnostic Operations, Inc.

(57) ABSTRACT

Described are a device and a method for the manipulation of a liquid sample material in which magnetic microparticles are suspended whereby the microparticles have a functionalized surface and an analyte is bound to the surface. The sample material is introduced into a device with a liquid system through an injection device (50) and in a first mobile phase the sample material is carried to an extractor (90). In a section (97) of the extractor (90) the microparticles are immobilized by means of a magnetic field of a controllable means (96) and separated from the remaining sample material. By switching over of a switching unit (110) a second mobile phase (75) is carried to the extractor (90) and the second mobile phase (75) detaches the adsorbed analyte from the surface of the microparticles. The second mobile phase (75) with the dissolved analyte(s) can be analyzed by way of chromatographic separation (130) and subsequent detection (140).

13 Claims, 19 Drawing Sheets

U.S. PATENT DOCUMENTS

| | | |
|---|---|---|
| 2002/0036141 A1 | 3/2002 | Gascoyne et al. |
| 2003/0168392 A1 | 9/2003 | Masuda et al. |
| 2008/0217254 A1 | 9/2008 | Anderson |
| 2010/0291712 A1* | 11/2010 | Vogeser .................. 436/526 |

FOREIGN PATENT DOCUMENTS

| | | |
|---|---|---|
| EP | 2068143 A1 | 6/2007 |
| WO | 2007095919 A1 | 1/2007 |
| WO | 2007020294 A1 | 2/2007 |

OTHER PUBLICATIONS

Franzreb et al., "Protein Purification Using Magnetic Absorbent Particles," Appl Microbiol Biotechnol (2006), 70: 505-516.

Vogeser et al., "Determination of Itraconazole and Hydroxyitraconazole in Plasma by Use of Liquid Chromatography-Tandem Mass Spectrometry with On-Line Solid-Phase Extraction," Clin Chem Lab Med 2003; 41(7): 915-920.

* cited by examiner

Fig. 3 A, B
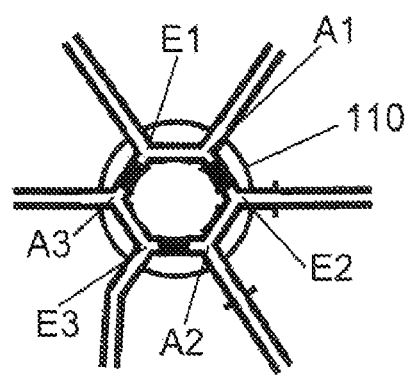
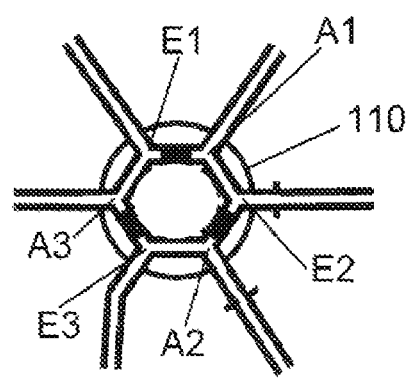
(I)  (II)
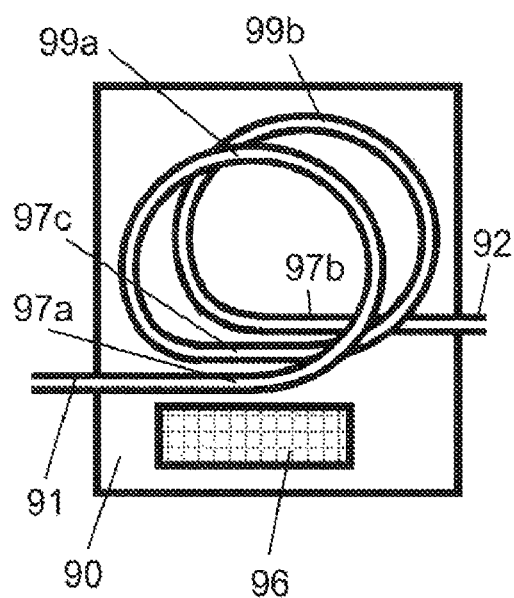

Fig. 10 A, B
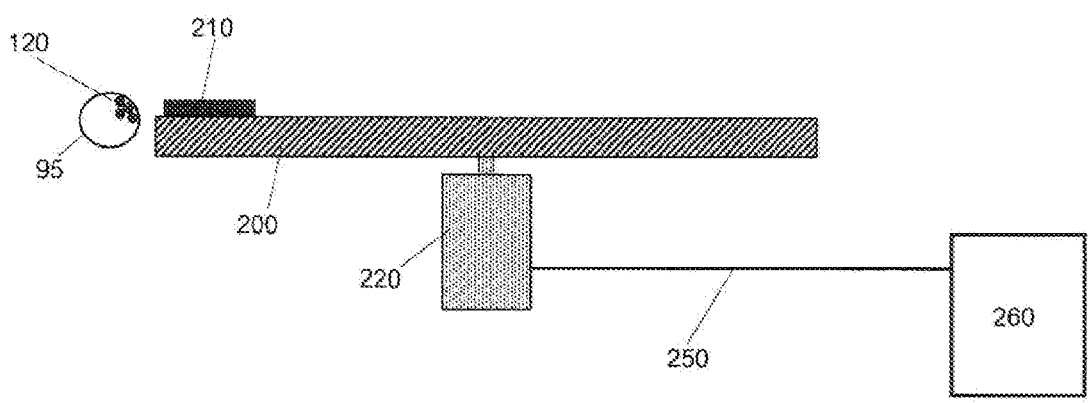
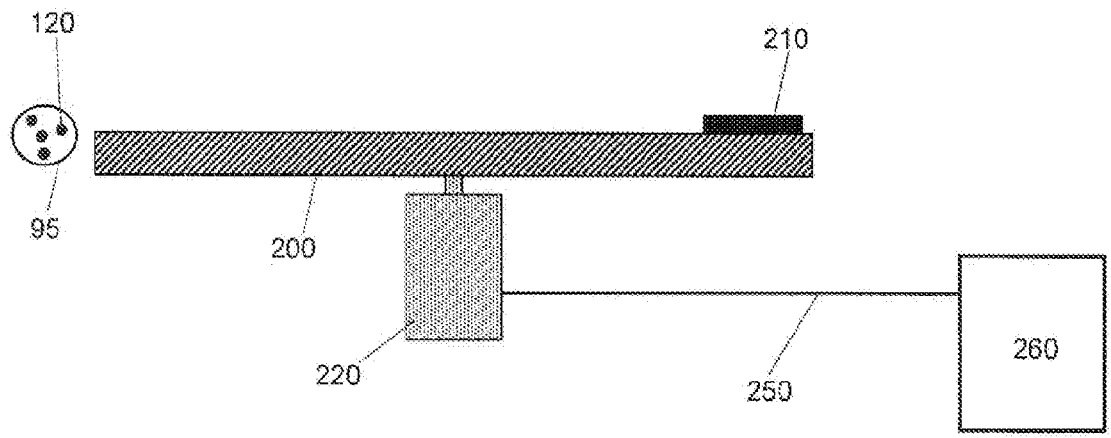

Fig. 18 A, B
A
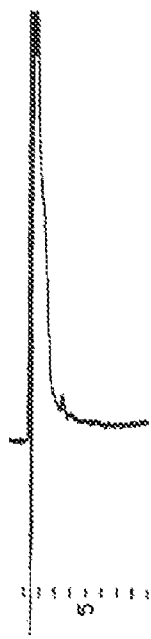
B
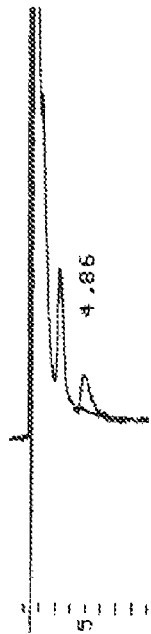

MANIPULATION OF MAGNETIC MICROPARTICLES IN A HIGH PRESSURE LIQUID SYSTEM AND EXTRACTION PROCESS

RELATED APPLICATIONS

This application is a continuation-in-part of U.S. Ser. No. 12/328,228 filed Dec. 4, 2008 and claims priority to European application EP 08021311.9 filed Dec. 8, 2008.

FIELD OF THE INVENTION

The present invention concerns the automation of extraction processes by means of magnetic microparticles with a functionalized surface. Particularly, the invention concerns a device and a method for the manipulation of a liquid sample material in which magnetic microparticles are suspended whereby the microparticles have a functionalized surface and an analyte is bound to the surface. The sample material is introduced into a device with a liquid system through an injection device (50) and in a first mobile phase the sample material is carried to an extractor (90). In one or more sections (97) of the extractor (90) the microparticles are immobilized by means of a magnetic field of a controllable means (96) and separated from the remaining sample material. By switching over of a switching unit (110) a second mobile phase (75) is carried to the extractor (90) and the second mobile phase (75) detaches the adsorbed analyte from the surface of the microparticles. The second mobile phase (75) with the dissolved analyte(s) can be analyzed by way of chromatographic separation (130) and subsequent detection (140) of the analyte(s).

BACKGROUND

US 2003/0168392 A1 discloses a multi-dimensional liquid chromatograph separation system. The analytes are separated on a first analysis system consisting of a first column and a first mobile phase, and are trapped on trapping columns. The trapped analytes are subsequently loaded onto the second analysis system consisting of a second column and a second mobile phase. The document discloses the trapping and loading mechanism consisting of a combination of switching valves necessary to produce the serial separations.

An overview on the purification of proteins using magnetic adsorbent particles is given by Franzreb M., et al. Appl. Microbiol. Biotechnol. 70 (2006) 505-516. Particularly, Hubbuch, J. J., et al. Biotechnol Bioeng 79 (2002) 301-313 describe a high-gradient magnetic separation system comprising a filter chamber filled with woven wire mesh of steel, whereby the filter chamber is positioned between the plane pole shoes of an electromagnet which can be switched on or off. The filter chamber comprises two openings at opposite ends, at the top and the bottom of the chamber. The two openings of the filter chamber are fluidically connected and a pump is integrated in the fluidic connection. Thereby a loop is formed such that a liquid phase can be cycled within the loop. Between the pump and the bottom opening of the chamber the authors disclose a three way valve, suitable for fluidically connecting the filter chamber with a batch reactor and a first buffer reservoir. Between the pump and the top opening of the filter chamber a four way valve is disclosed, the valve being suitable for making a fluidic connection with a second or a third buffer reservoir, or a fraction collector. The authors further disclose the use of such a fluidic system for purifying trypsin from crude pancreatin. To this end, magnetic particles functionalized with benzamidine are incubated in the batch reactor with a suspension of crude pancreatin, whereby trypsin is adsorbed to the particles. The suspension with the magnetic particles is fed into the loop together with binding buffer. The suspension is circulated in the loop and passed through the filter chamber several times with the electromagnet being switched on, whereby the magnetic particles are immobilized in the filter chamber. Subsequently, the liquid phase is exchanged by a washing buffer, the immobilized magnetic particles are released by switching the magnet off, and circulated in the loop with the washing buffer. During the washing step trypsin remains adsorbed to the magnetic particles. After a further immobilization step, the washing buffer is substituted with an elution buffer and elution is performed by again releasing the magnetic particles and circulating buffer and particles in the loop. The last step is the recovery of the elution buffer with trypsin from the system while the magnetic particles are retained in the filter chamber.

WO 2007/009519 discloses a system in which the separation chamber comprises, between two fits, a fluidic-bed of functionalized magnetic particles. A magnetic field can be applied and as a result the magnetic particles are immobilized at the walls of the separation chamber. A liquid phase containing an analyte is circulated through the separation chamber. Washing and elution steps can be performed.

US 2008/0217254 discloses a magnetic trap in a fluid handling system additionally comprising a plurality of rotary valve switching units. The magnetic trap comprises a plurality of pairs of magnets. A pair comprises two magnets which are placed side by side in opposite orientation, generating a magnetic field gradient. Several such pairs of magnets are positioned on a rotary device. A tube being part of the fluid system is positioned in a circular arrangement and in close proximity to the magnets such that high magnetic field gradients are applied to the lumen of the tube. When the device rotates the magnets, the magnetic field gradients are moved along the tube lumen. The device can be rotated clockwise or counterclockwise. Magnetic beads are trapped in the tube lumen. Movement of magnetic beads in the tube lumen of the trap is controlled by the movement of the magnetic field gradients.

For the majority of in-vitro diagnostic analyses it is necessary to extract one or more target analytes from complex sample materials (serum, plasma, whole blood, urine etc.). In this connection the respective target analytes are concentrated by different processes whereas components of the sample matrix which would hinder the subsequent analysis (e.g. proteins, peptides, salts) are depleted. The following extraction methods have been previously used to concentrate target analytes: protein precipitation with organic solvents or acids; liquid-liquid extraction (solvent extraction) with an evaporation step; solid phase extraction on cartridges which contain particles with defined surface structures (especially hydrocarbon-functionalized silica particles; solid phase extraction, SPE).

Extraction methods known from the prior art require a large amount of manual work. Methods for automating such extraction processes have up to now been technically very elaborate and have numerous disadvantages. They require, on the one hand, very demanding mechanical constructions e.g. pipetting systems and/or vacuum systems. On the other hand, the known methods require a large amount of solid and liquid consumables e.g. extraction cartridges, extraction plates, solvents. Furthermore, they require a long processing period and are characterized by a low sample throughput and limited series lengths.

An important aim of the work towards the present invention was to develop an extraction system which, in combination with a separation and analytical system, forms a substantially closed system. The liquid system according to the invention which is preferably a high pressure liquid system overcomes the limitations of current automated extraction processes. A particular object of the invention was to overcome and simplify certain disadvantages concerning the manipulation of magnetic or paramagnetic particles during the extraction process.

SUMMARY OF THE INVENTION

A general aspect of the invention is a device for the separation of magnetic or paramagnetic microparticles and the elution of an analyte adsorbed on said particles, the device being a liquid system (LS) comprising means for making fluidic connections (30), a first and a second inlet (10, 20), a rotary valve switching unit suitable for producing two different fluid connecting states (110), and an extractor (90) with an entry port (91) and an exit port (92), and with a controllable means (96) which can be used to temporarily apply a local magnetic field, characterized in that the extractor comprises a fluid connecting line (95) between the entry port (91) and the exit port (92), and the controllable means (96) is capable of temporarily applying a local magnetic field to two or more consecutive sections (97) of the line (95).

A further aspect of the invention is a device with a liquid system (LS) comprising means for making fluidic connections (30), a first and a second inlet (10, 20), at least one pressure-generating means (40), an injection device (50), two storage containers (60, 70) for a first and a second mobile phase (65, 75) in a liquid state of aggregation, a collecting vessel (80), an extractor (90), an outlet (100) and a means suitable for producing two different fluid connecting states (switching unit (110), characterized in that the first inlet (10) is designed such that the first mobile phase (65) can be fed under pressure from the first storage container (60) to the LS via a fluidic connection; the first inlet (10) is additionally fluidically connected to an injection device (50), the injection device being designed such that it allows a mixture (120) of liquid sample material (121) and microparticles suspended therein (122) to be introduced into the first mobile phase that was introduced through the inlet; the second inlet (20) is designed such that the second mobile phase (75) can be fed under pressure from the second storage container (70) to the LS via a fluidic connection; the first inlet (10) is connected to a first entry port (E1) of the switching unit (110) and the second inlet (20) is fluidically connected to a second entry port (E2) of the switching unit; the extractor (90) has one entry port (91) and one exit port (92) where the entry port (91) of the extractor is fluidically connected to a first exit port (A1) of the switching unit and the exit port (92) of the extractor is fluidically connected to a third entry port (E3) of the switching unit; the extractor additionally comprises a fluid connecting line (95) between the entry port (91) and the exit port (92), also a controllable means (96) which can be used to temporarily apply a local magnetic field to two or more consecutive sections (97a, 97b) of this line; the second exit port (A2) of the switching unit (110) is the outlet (100) or is fluidically connected to the outlet (100); the third exit port (A3) of the switching unit (110) is fluidically connected to the collecting vessel (80); and the switching unit (110) is suitable in a first connecting state (I) for fluidically connecting E1 and A1, E2 and A2 as well as E3 and A3 and in the second connecting state (II) it is suitable for fluidically connecting E2 and A1, E3 and A2 as well as E1 and A3.

Yet, a further aspect of the invention is the use of the device according to the invention for the manipulation of magnetic microparticles and two different mobile phases in a liquid state of aggregation.

Yet, a further aspect of the invention is a method for obtaining a purified analyte from a complex liquid sample material containing the said analyte comprising the steps (a) contacting the liquid sample material (121) containing the analyte with microparticles (122) made of a magnetic or paramagnetic material with a functionalized surface (123) whereby the analyte adsorbs to the surface; followed by (b) introducing the sample material with the microparticles into a device according to the invention using the injection device (50); followed by (c) pumping a first mobile phase (65) from a first storage vessel (60) into the first inlet (10) of the device where the switching unit (110) of the device makes the connecting state (I) and in the extractor (90) a magnetic field is applied to a first section (97a) of the line (95) located therein which is suitable for immobilizing the magnetic or paramagnetic microparticles (122) contained in the mobile phase entering through the line (95) on the nearest inner wall (93) of the line (95) facing the magnetic field in the first section (97a); followed by (d) immobilizing the microparticles (122) in the extractor (90) in the first section (97a) of the inner wall (93) of the line (95); followed by (e) separating the microparticles (122) from the remaining sample material by further pumping the first mobile phase (65) from the first storage vessel (60) into the first inlet (10) whereby the immobilized microparticles are washed and the remaining sample material is fed into the collecting container (80); followed by (f) switching over the switching unit (110) into the connecting state (II) and pumping a second mobile phase (75) from the second storage vessel (70) into the second inlet (20) of the device where the second mobile phase (75) is suitable for detaching the adsorbed analyte from the surface of the microparticles (122); followed by (g) eluting the analyte by contacting the microparticles (122) with the second mobile phase (75) and at the same time weakening or removing the magnetic field from the first section (97a) of the line (95) in the extractor (90) and moving the microparticles (122) in the line (95) towards a second section (97b) of the line (95) by the movement of the mobile phase (75); (h) applying a magnetic field to the second section (97b) of the line (95) where the magnetic field is suitable for immobilizing magnetic or paramagnetic microparticles (122) contained in the mobile phase entering through the line (95) on the nearest inner wall (93) of the line (95) facing the magnetic field in the second section (97b); followed by (i) immobilizing the microparticles (122) on the inner wall (93) in the second section (97b) of the line; followed by (k) moving the second mobile phase containing the eluted analyte to the outlet (100) of the device by further pumping the second mobile phase (75) from the second storage vessel (70) into the second entry port (20) by means of which the analyte is obtained in a purified form at the outlet (100).

Yet, a further aspect of the invention is a method for detecting an analyte in a complex liquid sample material containing the said analyte comprising the steps (a) providing a device which is characterized in that the outlet (100) of the HLS is fluidically connected to a separation unit (130) and the separation unit is fluidically connected to a detector (140), and the exit port (145) of the detector is fluidically connected to the collecting vessel (80). (b) Preparing the purified analyte from the sample material using a device according to the invention wherein the analyte is obtained in a purified form at the outlet (100) of the device and the switching unit (110) makes the connecting state (II); (c) moving the second mobile phase containing (i) the analyte and (ii) optionally further substances eluted together with the analyte through the separation unit (130) and into the detector (140) where the movement is driven by pumping the second mobile phase (75) from the second storage vessel (70) into the second entry port (20); (d) detecting the analyte by the detector (140).

DESCRIPTION OF THE FIGURES

FIG. 3: A—Enlarged section from FIG. 1 and FIG. 2 which shows the two connecting states that can be made by the switching unit (110). In state (I) A1 and E1, A2 and E2 as well as A3 and E3 are simultaneously fluidically connected; in state (II) A3 and E1, A1 and E2 as well as A2 and E3 are simultaneously fluidically connected. B—Particularly preferred form of the extractor (90) in which the line (95) between the entry port (91) and exit port (92) of the extractor (90) has a helical configuration with two or more windings (99a, 99b) where one or more sections (97c) of the windings and the respective sections (97a, 97b) of the line leading to the entry port (91) and exit port (92) are arranged side by side.

Figure 1:
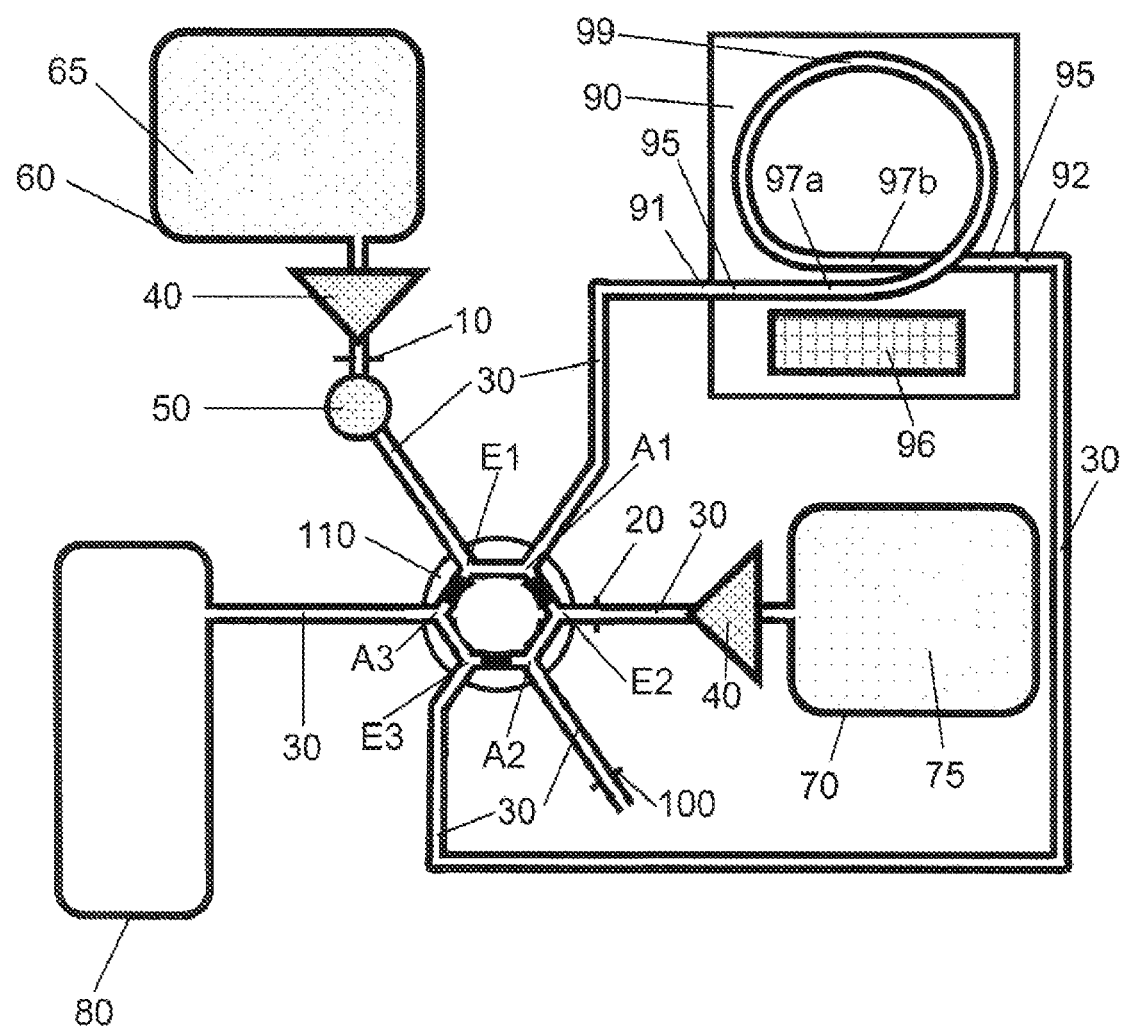
FIG. 1: Device with a liquid system (LS) comprising means for making fluidic connections (30), a first and a second inlet (10, 20), at least one pressure-generating means (40), an injection device (50), two storage containers (60, 70) for a first and a second mobile phase (65, 75) in a liquid state of aggregation, a collecting vessel (80), an extractor (90), an outlet (100) and a means suitable for producing two different fluid connecting states (switching unit, 110). In the preferred embodiment shown the pressure-generating means consists of two pumps which are each arranged between the storage container and inlet. Alternatively it would be possible to pressurize the storage container. In the extractor (90) the line (95) between the entry port (91) and exit port (92) of the extractor (90) has a helical configuration with one winding (99) where each of the sections (97a, 97b) of the line leading to the entry port and exit port are arranged side by side. The sections of the line labeled (97a) and (97b) leading to the entry port (91) and exit port (92) of the extractor are also referred to as a whole as (97).

A—A magnetic field mediated by the means (96) (symbolized by the horizontal texture of (96)) is applied to the area (97a) and immobilizes the extraction particles with the adsorbed substances to the side of the inner wall (93) of the line (95) facing the magnetic field. At the same time the first mobile phase (65) together with the remaining sample material is moved towards the outlet of the extractor and the collecting vessel (80). During this operating step the extraction particles are separated from the remaining sample material. Since in this process additional first mobile phase is continuously pumped into the LS, the particles are finally completely surrounded by the first mobile phase.

B—Subsequently the extraction particles with the adsorbed analyte are brought into contact with the second mobile phase and the magnetic field is switched off (or sufficiently reduced) so that the extraction particles are again mobilized by the flow of the second mobile phase in the line (95) and reach the loop (99). This area is shown in which the adsorbed substances (124, 125) are in the process of being detached from the extraction particles (122). This process takes place continuously while the extraction particles pass through the loop (99).

C—Subsequently the extraction particles are transported by the flow of the second mobile phase (75) through the line (95) to the area (97b) where they are again immobilized by a magnetic field (generated using (96)). The substances detached from the extraction particles including the analyte are now present in a purified form in the second mobile phase. They are subsequently again transported in the direction of flow in order to for example pass through an analytical separation device and a detector.

FIG. 6: Schematic representation of the process of sample purification by means of the device according to the invention shown in FIG. 2. The elements of the device that are shown correspond exactly to the elements shown in FIGS. 1, 2 and 3 and described in relation thereto. The steps shown in A-D are described in Example 1.

Figure 7:
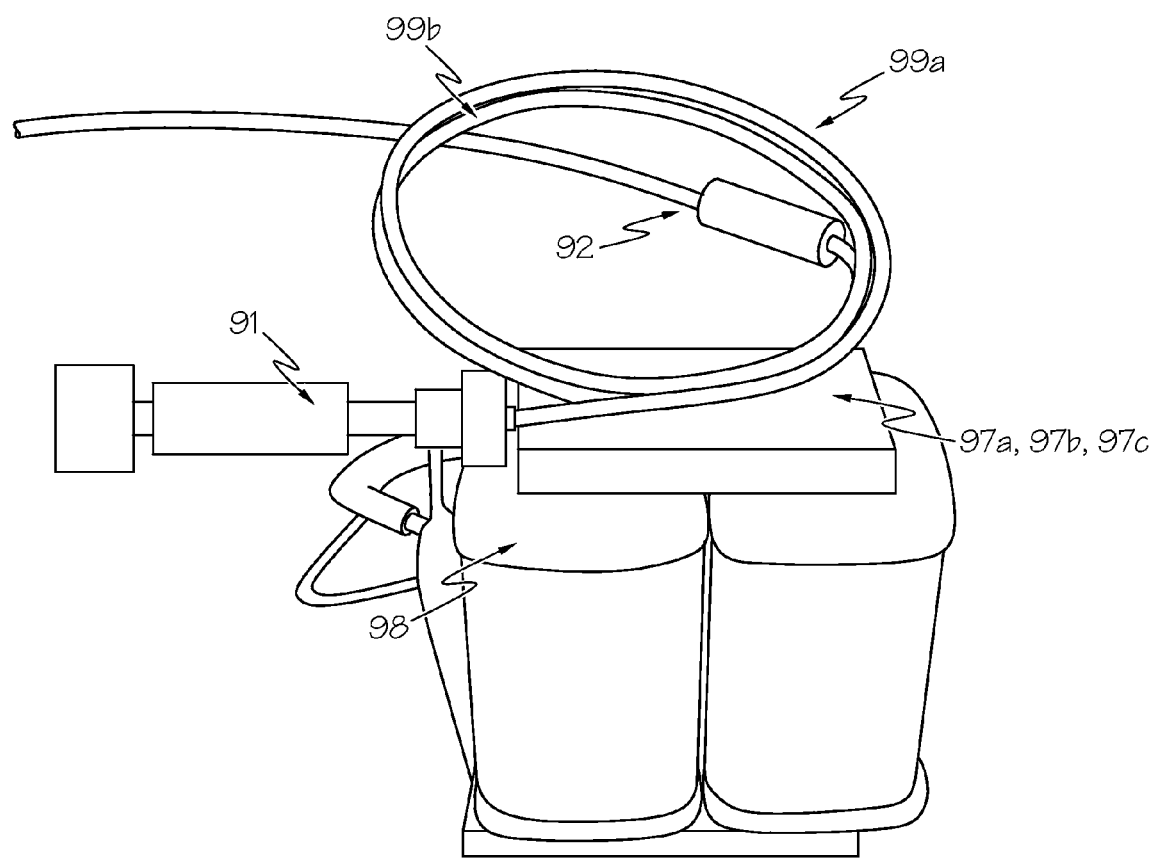

FIG. 7: A possible and preferred embodiment of the extractor comprises an electromagnet with a toroidal core transformer (98). The electromagnet can for example be actuated by a control device where the control device preferably also sets the switching states of the switching unit (110). The loop of the line of the extractor is configured in the form of a first and second winding (99a, 99b). Further windings can be added to increase the holding time of the extraction particles in the loop. The line that is actually used in this extractor consists of a HPLC tube made of polyphenyl sulfone (PPSU). The entry port (91) and exit port (92) of the extractor are provided with couplings. In the example shown there are three areas in which the extraction particles can be immobilized by applying a magnetic field, 97a, 97b and 97c.

Figure 8A:
Figure 8B:
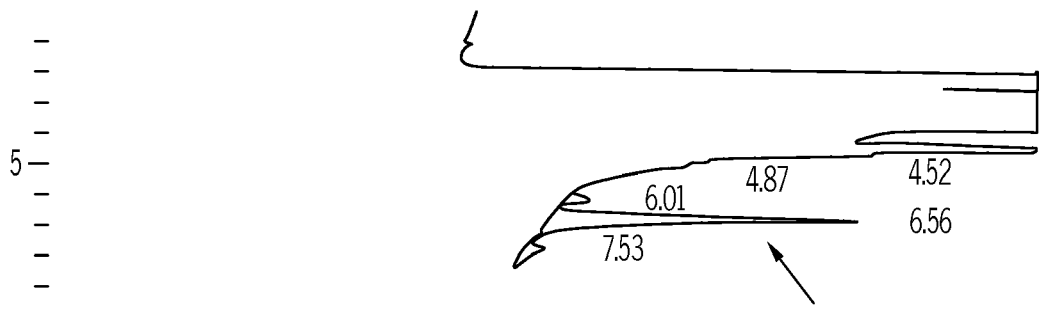
Figure 8C:
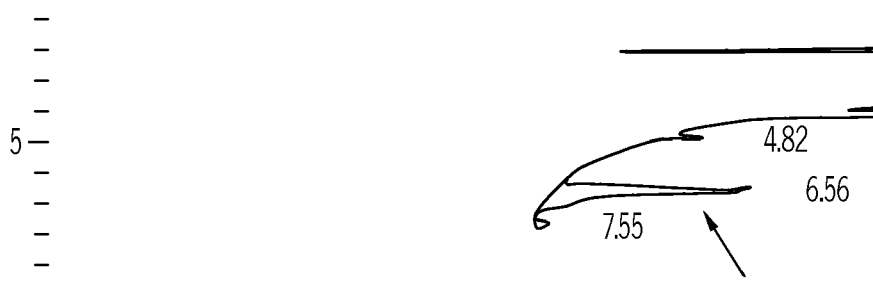

FIG. 8: Examples of chromatograms of samples which were processed and analyzed with the aid of a high-pressure liquid system according to the invention with an attached separation and detection unit (see Example 3). The X axis shows the retention time and the Y axis shows the absorption measured on the UV spectrometer.

A—Chromatogram of a "drug-free" patient sample.

B—Chromatogram of the calibrator sample with a set itraconazole concentration of 2.9 mg/l. The peak area comprises 81234 counts and the retention time is 6.56 min.

C—Chromatogram of the analyzed patient sample. The determined itraconazole concentration is 2.0 mg/l. The peak area comprises 56352 counts and the retention time is 6.56 min.

Figure 9A:
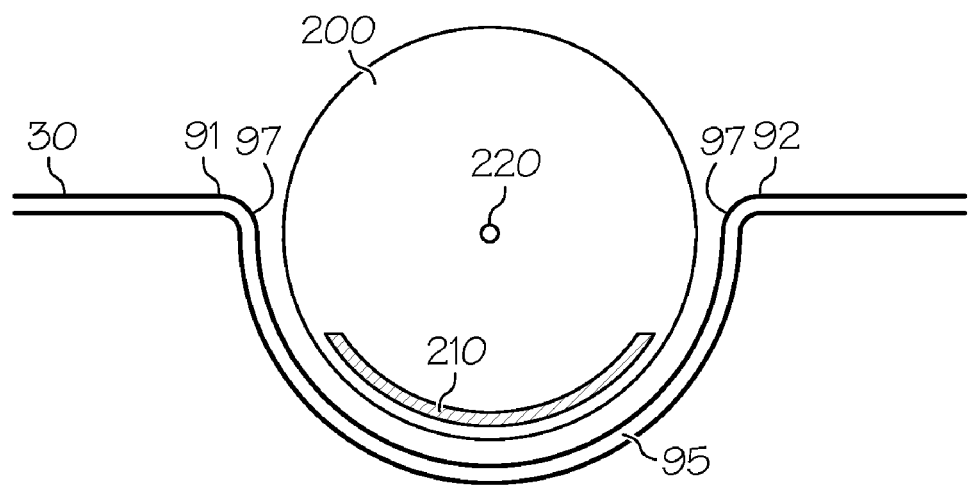
Figure 9B:
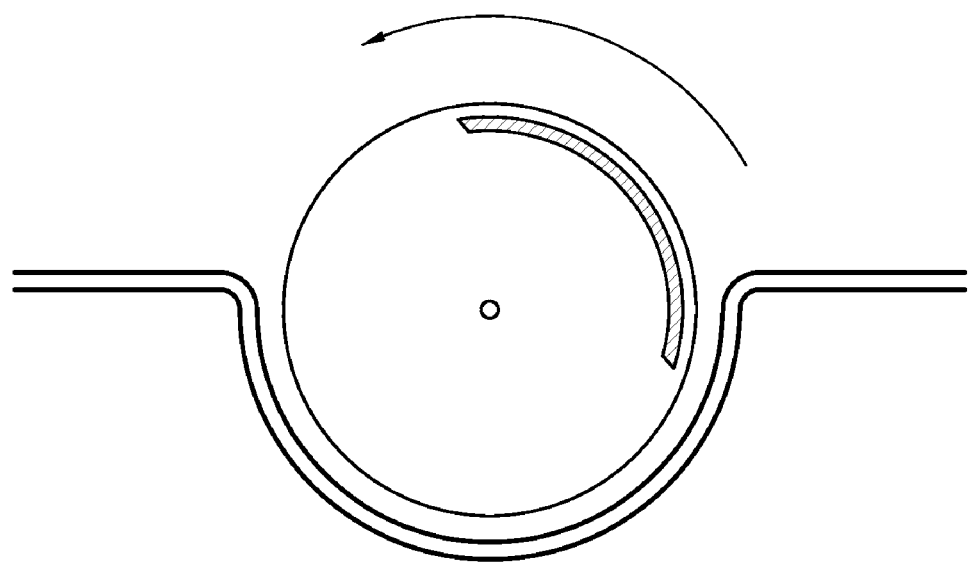

FIG. 9: Schematic representation of a particularly preferred embodiment of the extractor (90). The elements of the device that are shown correspond exactly to the elements shown in the previous Figures and described in relation thereto. The rotatable disk (200) is attached to agitating means (220) such that agitation results in rotational movement. A magnetic field is generated by one or more permanent magnets (210) located and attached in a sector of the disk, preferably close to the edge of the disk. In the configuration shown in (A) the magnetic field acts upon the line (95) in the section (97) between the entry port (91) and the exit port (92). As shown in B, rotational movement of the disk displaces the magnetic field such that the magnetic force acting upon the line (95) is reduced. Reduction is maximal when the one or more magnets are positioned opposite of their position in (A).

FIG. 10: Schematic representation of a cross-section of the extractor (90) depicted in FIG. 9. The elements of the device that are shown correspond exactly to the elements shown in the previous Figures and described in relation thereto. The agitator (220) is connected with a controlling device (260), preferably by means of a connecting cable (250).

In a first position of the disk (200) shown in (A) the one or more permanent magnets (210) are positioned close to the connecting line (95) such that the magnetic field extends through the space occupied by the line. Magnetic particles (120) present in the line (95) are attracted to the inner wall of the line and immobilized by the magnetic field.

Following rotation of the disk by 180° the one or more magnets are positioned on the opposite side, the magnetic force acting upon the magnetic particles is weakened and the particles are released, as shown in (B).

Figure 11:
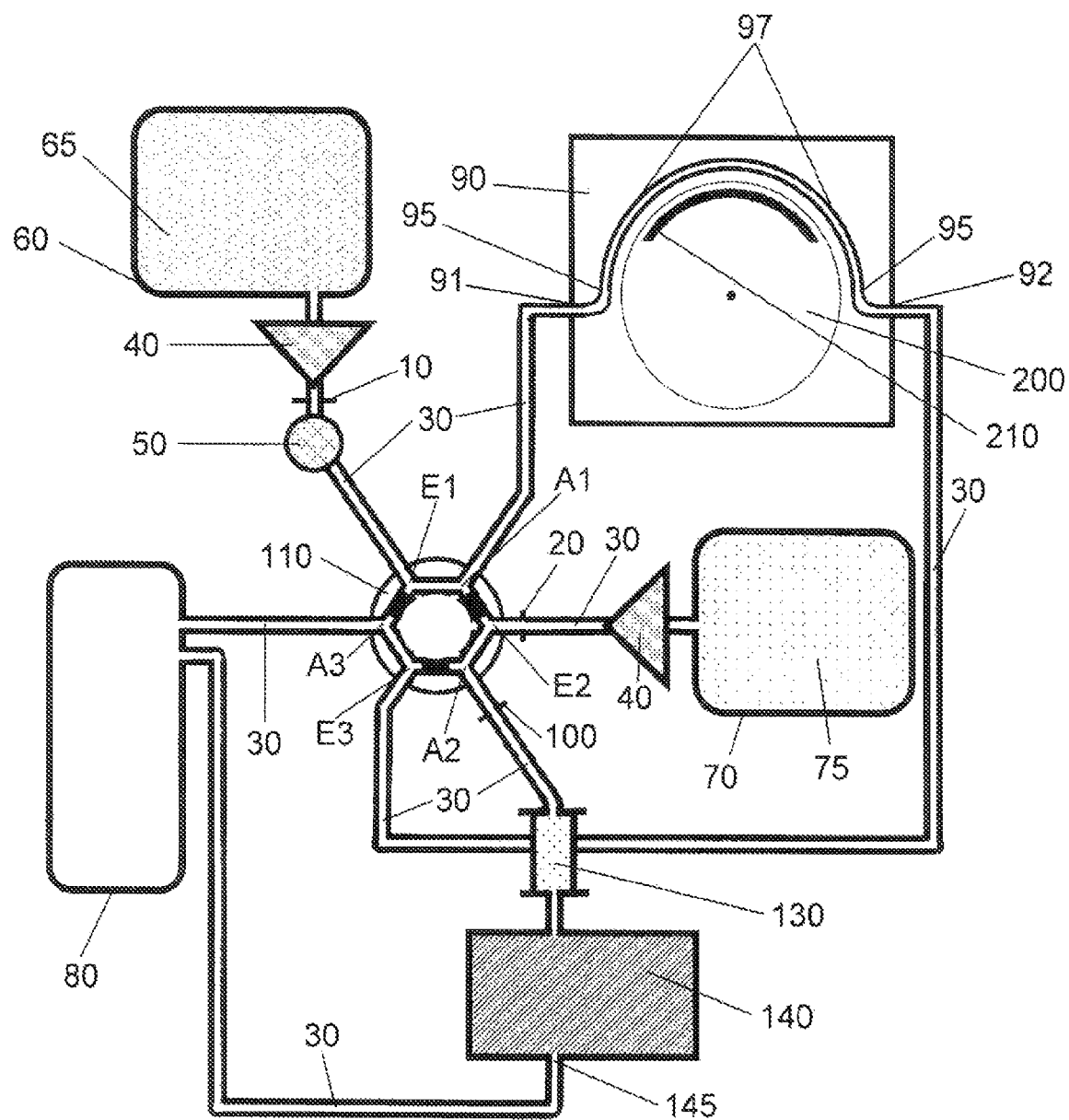
Figure 17:
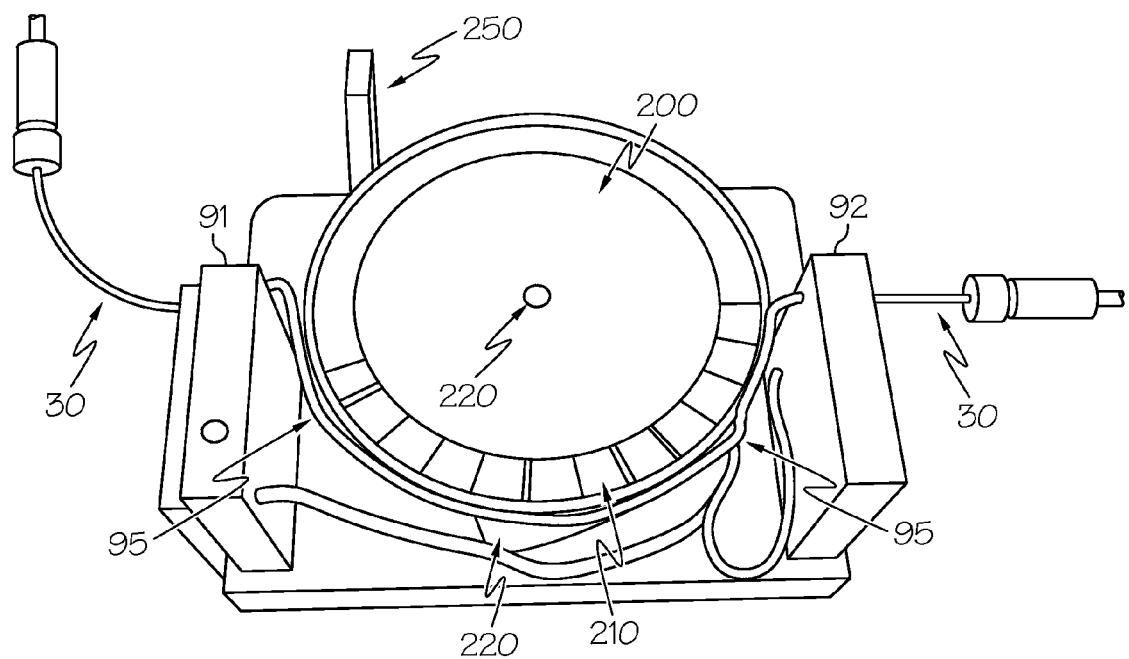

FIG. 11: A very much preferred embodiment of a device according to the invention and analogous to the devices shown in FIGS. 1 and 2, FIG. 2 in particular. The elements of the device that are shown correspond exactly to the elements shown in the previous Figures and described in relation thereto. The device comprises an extractor as shown in FIGS. 9, 10, and 17 and explained in the respective figure legends.

Figure 12:
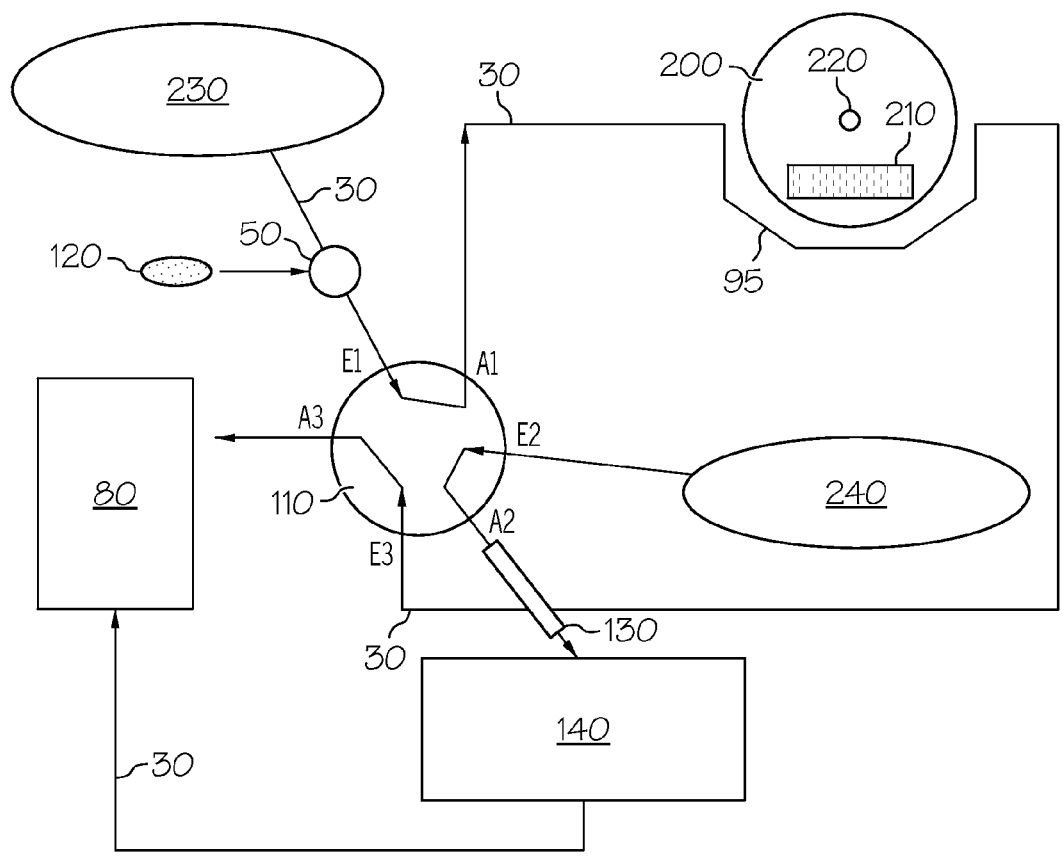

FIG. 12: Working principle of the device shown in FIG. 11. The subsequent stages of working cycle are demonstrated by FIGS. 11 to 16.

The elements of the device that are shown correspond exactly to the elements shown in the previous Figures and described in relation thereto. For simplicity, the reservoir with the first mobile phase and the first pressure generating means for transporting the first mobile phase into the liquid system are summarily referred to as element (230). Likewise, element (249) refers to the reservoir with the second mobile phase and the second pressure generating means. The above applies similarly to FIGS. 13-16.

A mixture of liquid sample material containing an analyte and also containing magnetic particles (120) is injected into the liquid system. The switching unit is in the first connecting state and the first mobile phase is pumped into the system.

Figure 13:
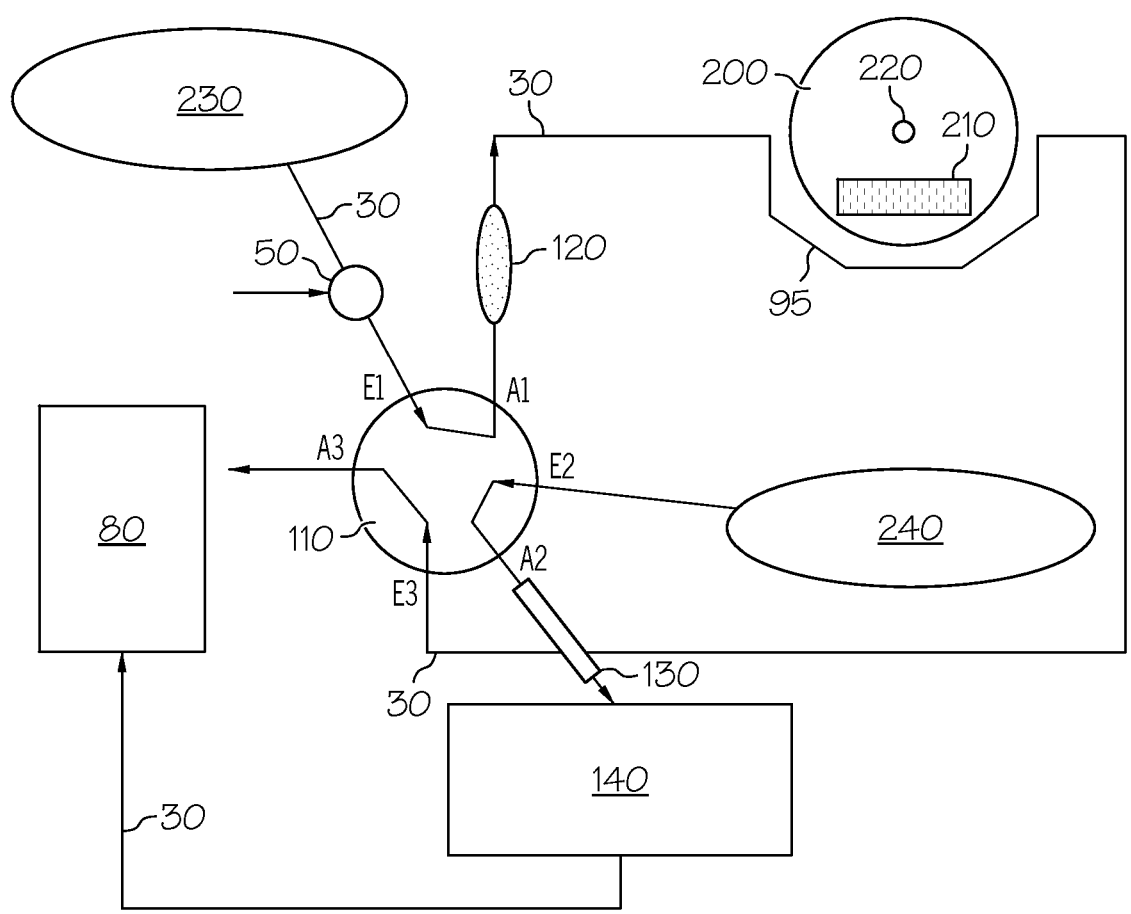

FIG. 13: The injected mixture (120) is transported by the flow of the first mobile phase towards the extractor. Before and during the transport the magnetic particles interact with the sample and the analyte is adsorbed on the functionalized surface of the particles.

The disk (200) with the one or more magnets is in a first position as shown in FIG. 10 A.

Figure 14:
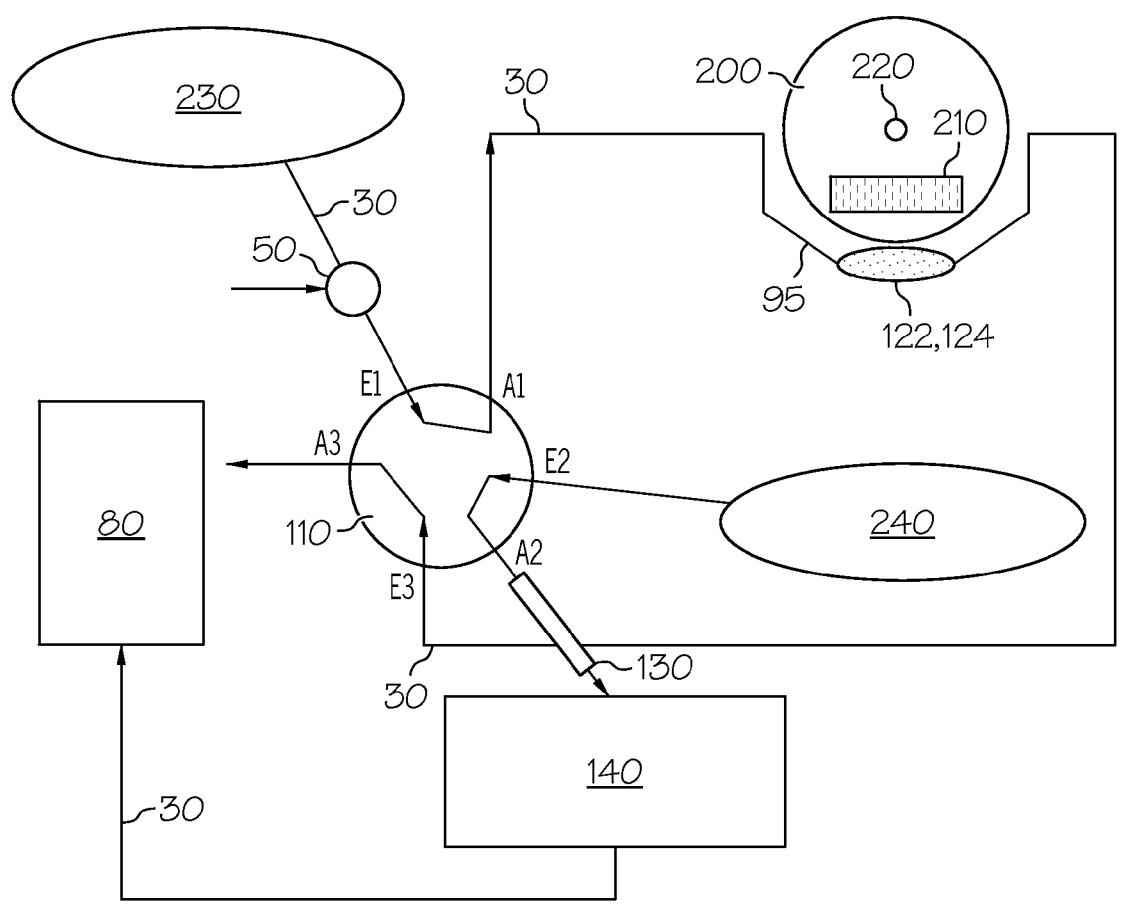

FIG. 14: When the mixture with magnetic particles reaches the line (95) the particles are immobilized by the magnetic force of the field generated by the magnet or magnets located in proximity to the line (95). The magnetic particles are immobilized on the inner wall of the line (95). This detail is also shown in FIG. 10 A. Once the particles are immobilized, further flow of the first mobile phase through the line (95) removes non-adsorbed components of the sample material (washing). As a result, magnetic particles (122) with the analyte(s) (124) adsorbed are separated and provided for the following extraction step.

Figure 15:
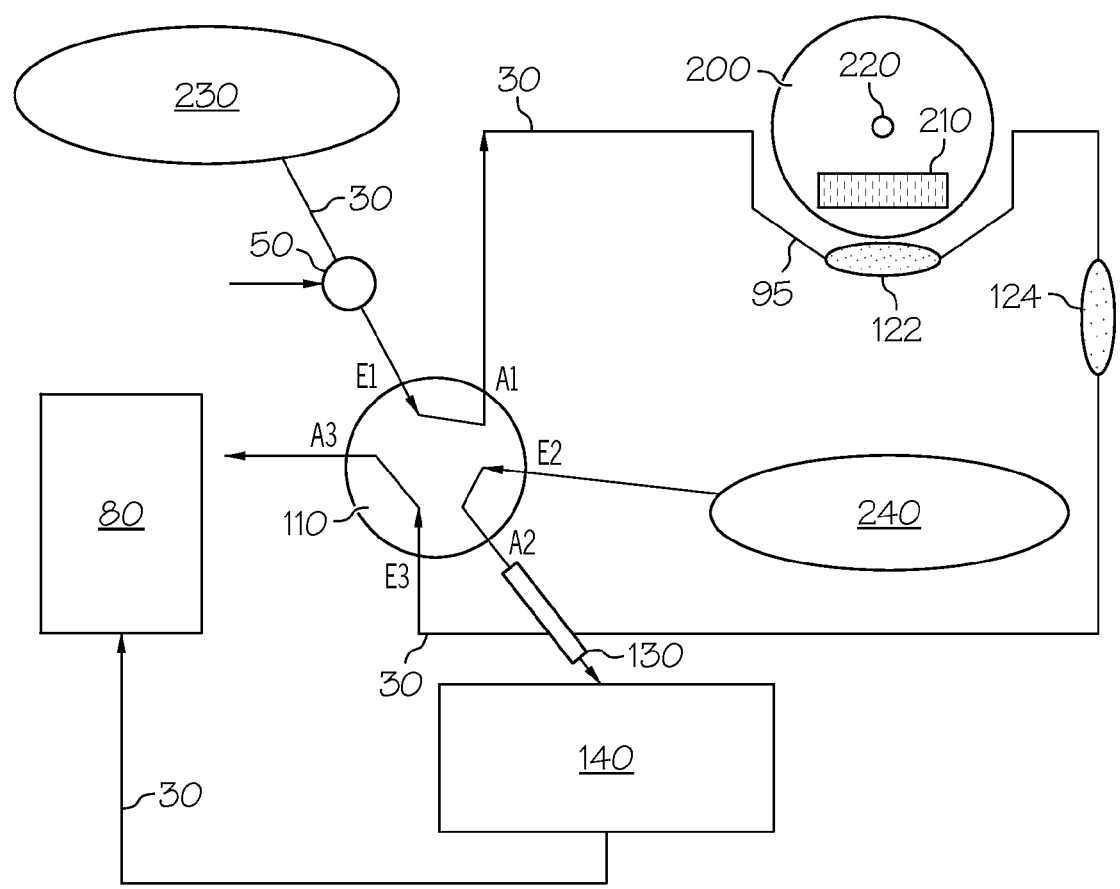

FIG. 15: For the extraction of the adsorbed analyte(s) the fluid connecting state of the switching unit (110) is switched to the second connecting state and the second mobile phase is pumped into the system. As the second mobile phase reaches the immobilized magnetic particles in the line (95) of the extractor (90) the adsorbed one or more analyte(s) (124) are eluted and transported to a separation unit (130) (e.g. a chromatographic column) which is attached to a detector (140). The Figure shows the eluted analyte(s) (124) already being transported by flow, downstream of the extractor. The magnetic particles (122) are held back in the extractor.

Figure 16:
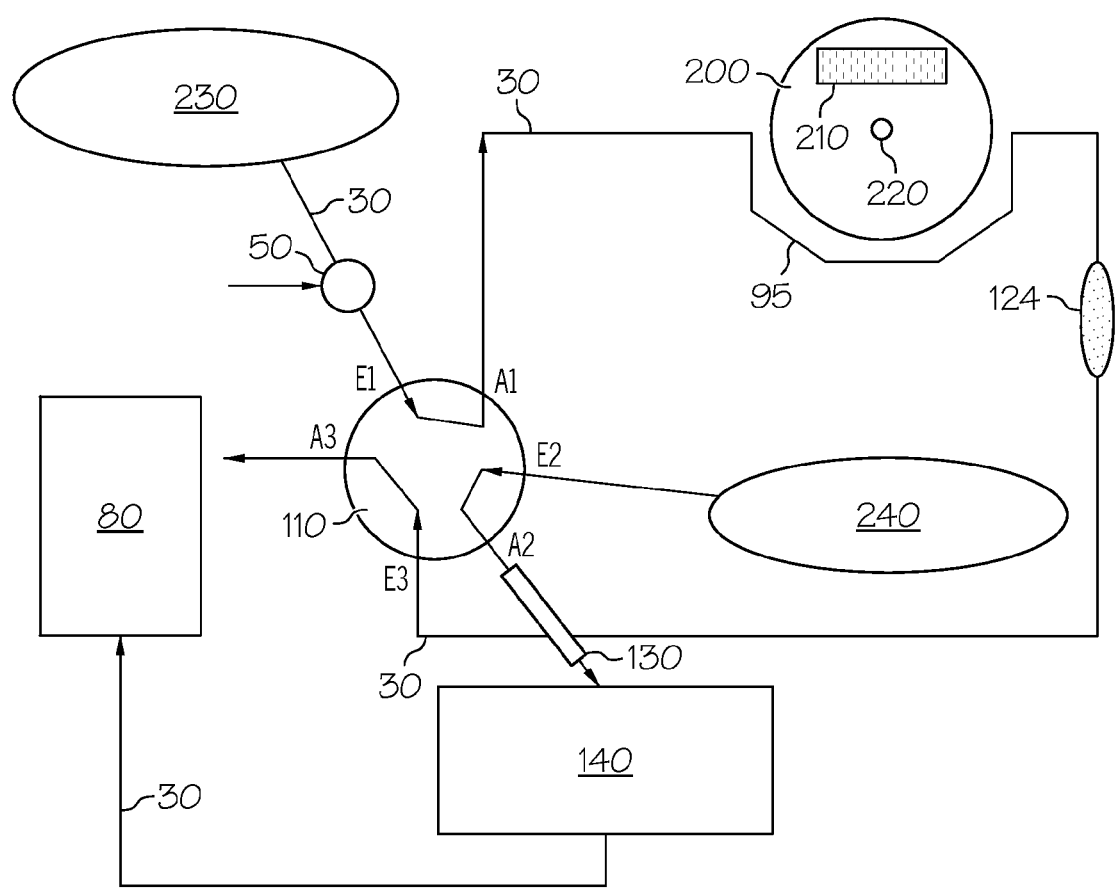

FIG. 16: Following analysis of the analyte(s) the liquid system is regenerated. The switching unit (110) is switched back to the first connecting state and the disk (200) in the extractor is adjusted in the second position. In this position the magnetic field is diverted from the line (95), also shown in FIG. 10 B. The magnetic particles become mobile again. The first mobile phase is pumped again into the system, thereby flushing the second mobile phase and the magnetic particles (122) into the waste reservoir (80).

FIG. 17: Picture of an extractor according to FIG. 9 and FIG. 10 A, B, whereby several magnets of cubic shape are positioned in a sector of the disk (200). The elements of the device that are shown correspond exactly to the elements shown in the previous Figures and described in relation thereto.

FIG. 18: Representative chromatograms of a quantitative analysis of itraconazole in human plasma using the magnetic particle extraction and the device according to FIG. 11 in the process shown and explained in FIGS. 12-16. Analyte was detected by a UV-detector. (A) blank plasma. (B) patient's plasma pool (itraconazole, 378 μg/l; the first peak corresponds to the drug metabolite hydroxyl-itraconazole, the peak eluting after 4.86 min corresponds to itraconazole.

DETAILED DESCRIPTION OF THE INVENTION

Certain terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth in this description of the present invention.

The term "comprising" is used in the description of the invention and in the claims to mean "including, but not necessarily limited to".

The articles "a" and "an" are used herein to refer to one or to more than one (i.e. to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by $n1 \leq x \leq n2$.

If not stated otherwise, it is understood that the term "about" in combination with a numerical value n indicates a value x in the interval given by the numerical value±5% of the value, i.e. $n-0.05*n \times n+0.05*n$. In case the term "about" in combination with a numerical value n describes a preferred embodiment of the invention, the value of n is most preferred, if not indicated otherwise.

The term "segment" refers to a circle segment, that is to say a continuous section of the circumference of a circle.

The invention provides a liquid system which can be used to manipulate magnetic or paramagnetic microparticles and two different mobile phases, preferably liquid phases. As an example the present invention is illustrated on the basis of the use of corresponding microparticles with a hydrocarbon-functionalized surface. Such microparticles have previously not been used for quantitative analyses in clinical chemistry. However, they have considerable advantages when preparing clinical sample material. These advantages are particularly manifest when the aim is to detect an analyte having a low molecular weight, typically between about 50 and about 1,000 Daltons (Da). Further preferred ranges of the molecular weight of the analyte(s) are between about 50 and about 800 Da, between about 50 and about 750 Da, between about 50 and about 600 Da, and between about 50 and about 500 Da. A person skilled in the art can profit from using such particles especially in a quantitative chromatographic analysis.

In a simple form of sample preparation, magnetic or paramagnetic microparticles (extraction particles) with hydrocarbon-functionalized surfaces are brought into contact with liquid sample material for example whole blood, serum, plasma or haemolysed blood in a reaction vessel. Subsequently the analyte is adsorbed from the liquid phase onto the functionalized surface of the particles. After a certain holding time the solid and liquid phases are separated from one another. This can preferably take place by removing the liquid phase from the vessel while the particles are retained in the vessel by a magnetic field. For example a permanent magnet can be moved from outside to the wall of the vessel such that the magnetic particles are immobilized at this site on the vessel inner wall. The particles can be subsequently washed. For this purpose the magnet can for example be removed and after that the particles are resuspended in a washing buffer. After a renewed immobilization of the particles and removal of the washing buffer, the analyte is eluted from the surface of the particles by contacting the microparticles with a solvent suitable for the desorption of the analyte. After separating the solid and liquid phases, the analyte can be detected from the solvent using chromatographic methods.

The direct automation of the manual operating steps as described above does not yet eliminate the disadvantages of the prior art in a satisfactory manner. In contrast, the present invention describes a method for automating the extraction in a liquid system, preferably a high pressure liquid system, which surprisingly has many advantages. In particular the device according to the invention requires a minimum of moving parts and thus makes the use of complicated pipetting units that can be moved in three dimensions or complicated vacuum system superfluous.

A particularly preferred embodiment of the present invention is a substantially closed high pressure liquid system and the use of the same to manipulate magnetic or paramagnetic microparticles suspended in a liquid sample material and two different mobile phases. A substantially closed system in the sense of the present invention is a high pressure liquid system in which there is no operationally open connection between the space filled by the mobile phase and the environment. The high pressure liquid system according to the invention is a substantially closed system because it has an injection device which allows a mixture of liquid sample material and extraction particles to be introduced in a controlled manner into the liquid system.

According to the invention two different mobile phases are used. The first mobile phase is selected such that it can be used to separate extraction particles and the remaining sample material. In this connection "remaining sample material" means the material from the liquid sample from which at least portions of the analyte contained therein have been extracted by adsorption to the extraction particles. The second mobile phase is used to detach the analyte from the extraction particles. In this connection it is preferred that the first and second mobile phase have a liquid state of aggregation or are each in a liquid state of aggregation in the liquid system according to the invention. This also implies the use of mobile phases which are volatile at room temperature and normal ambient pressure. In the liquid system according to the invention such a particular mobile phase is kept under conditions of temperature and/or pressure such that inside the liquid system the mobile phase is in a liquid state of aggregation.

When the liquid system according to the invention is used, the material that is introduced remains within the system from the time at which the mixture of extraction particles and sample material is injected until the chromatographic analysis of the analyte.

The described process allows magnetic or paramagnetic microparticles which are used for extraction for analytical purposes to be simply manipulated preferably in the high pressure liquid system according to the invention. An automated operation of the device according to the invention is readily possible. The principle of manipulating the microparticles allows analytical extraction systems to be constructed in which a minimum of moved components have to be used. In particular complicated x-y-z pipetting units or vacuum systems are no longer necessary in contrast to the previously common automated extraction systems. Moreover, the system according to the invention can be extremely compactly configured and the requirement for solid or liquid consumables is minimized. Furthermore, the closed system design allows the use of liquid phases with a relatively high vapour pressure which would lead to problems in open systems such as automated pipettors for example due to the build up of pressure by evaporation of the liquid phase in the pipetting chamber. Compared to previous systems, the system according to the invention also enables very short cycle times and thus a high sample throughput.

Figure 2:
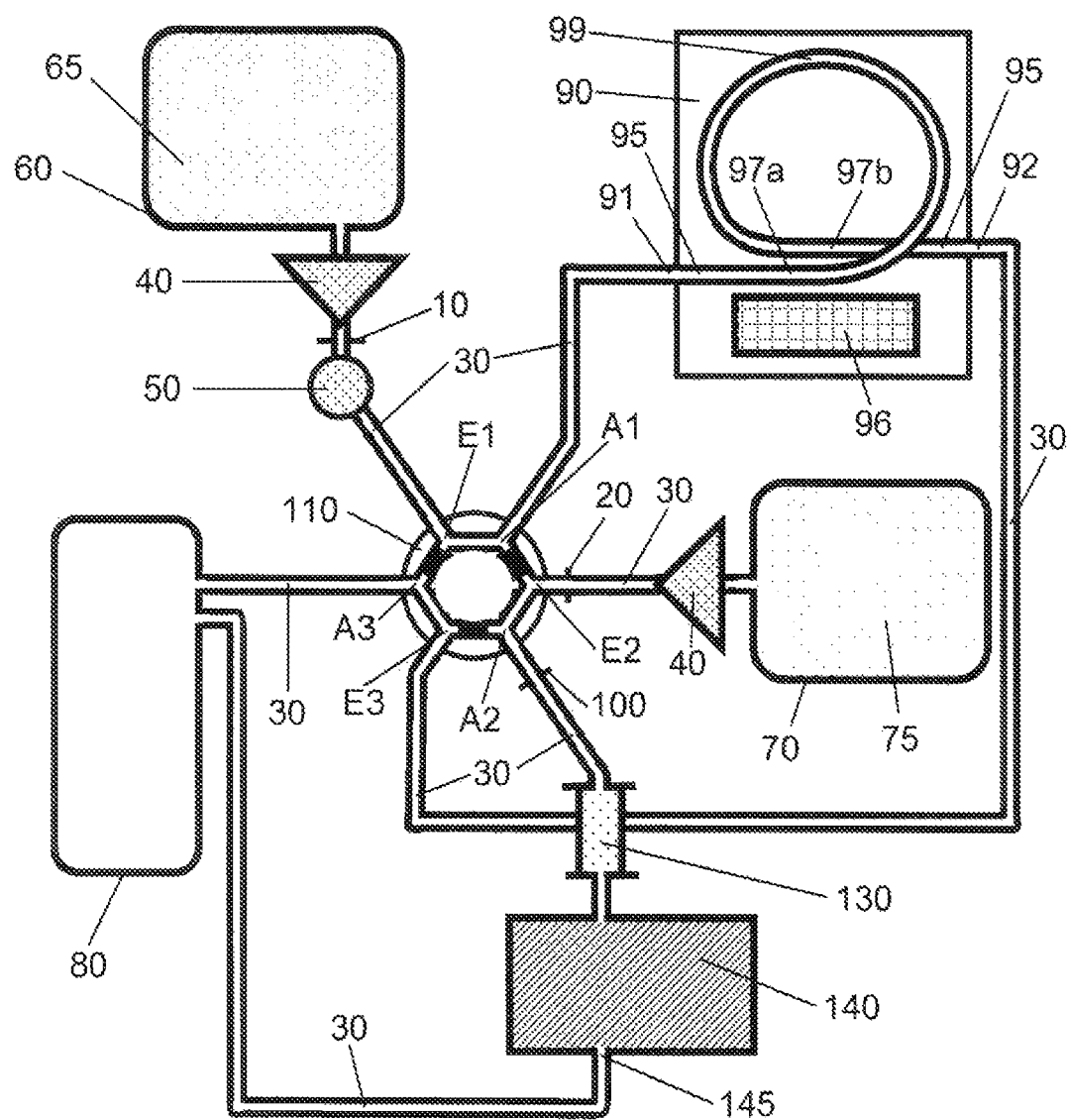
FIG. 2: Preferred high pressure LS (HLS) in which the HLS is a substantially closed system and the outlet (100) is fluidically connected to a separator unit (130) and the separating unit is fluidically connected to a detector (140) and the exit port (145) of the detector is fluidically connected to the collecting vessel (80). With regard to the extractor reference is made to the description of FIG. 1.
Figure 4:
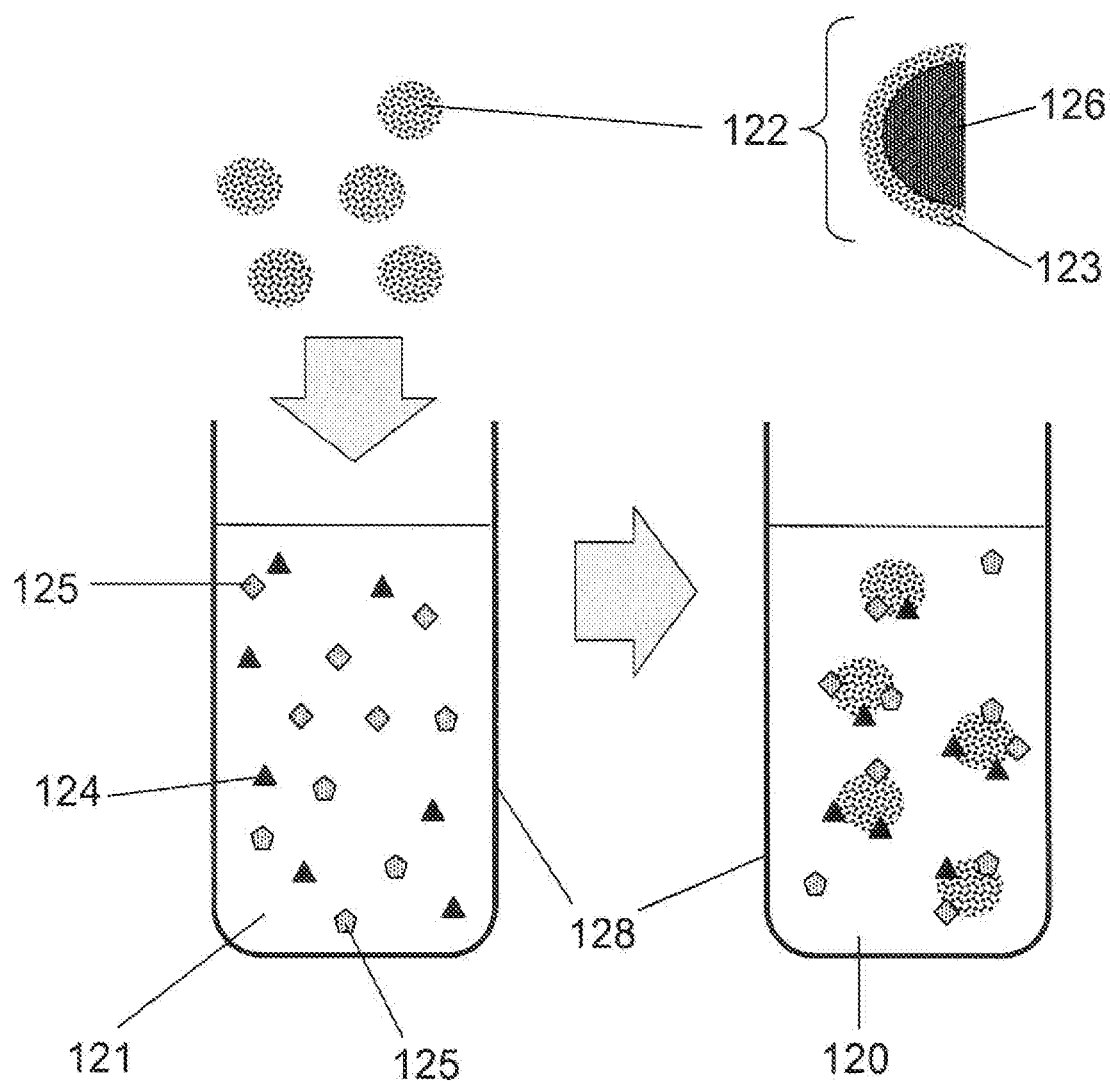
FIG. 4: Schematic representation of the extraction particles (122) and their use for the adsorption of the analyte (124) and optionally further substances (125) contained in the liquid sample material (121) which can adsorb to the surface (123) of the extraction particles. For this purpose the surface (123) of the extraction particles is functionalized e.g. in a particularly preferred embodiment it is coated at least partially with a hydrophobic layer. The core of the extraction particles contains a magnetic or paramagnetic material. The mixture (120) of sample material (121) and extraction particles (122) with adsorbed analyte (124) is introduced into the device according to the invention using the injection device (50) see FIG. 1 and FIG. 2.
Figure 5A:
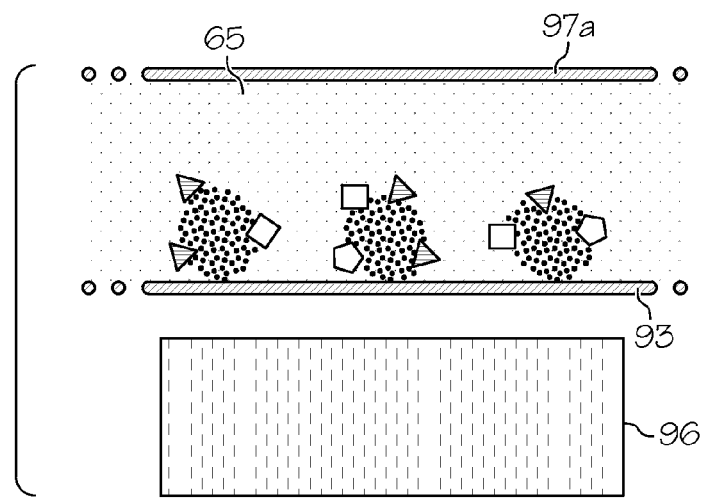
FIG. 5: Schematic representation of the action of the extractor (90).
Figure 5B:
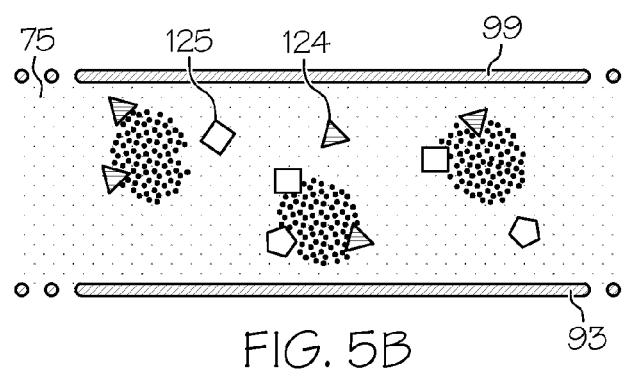
Figure 5C:
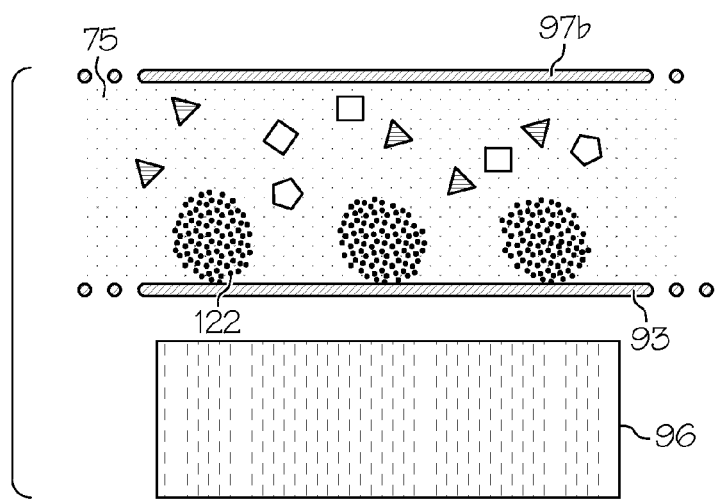
Figure 6A:
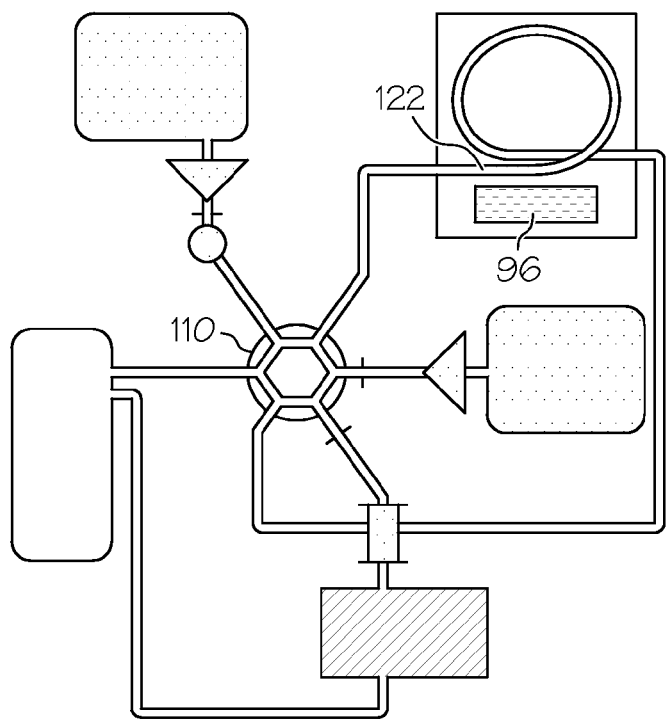
Figure 6B:
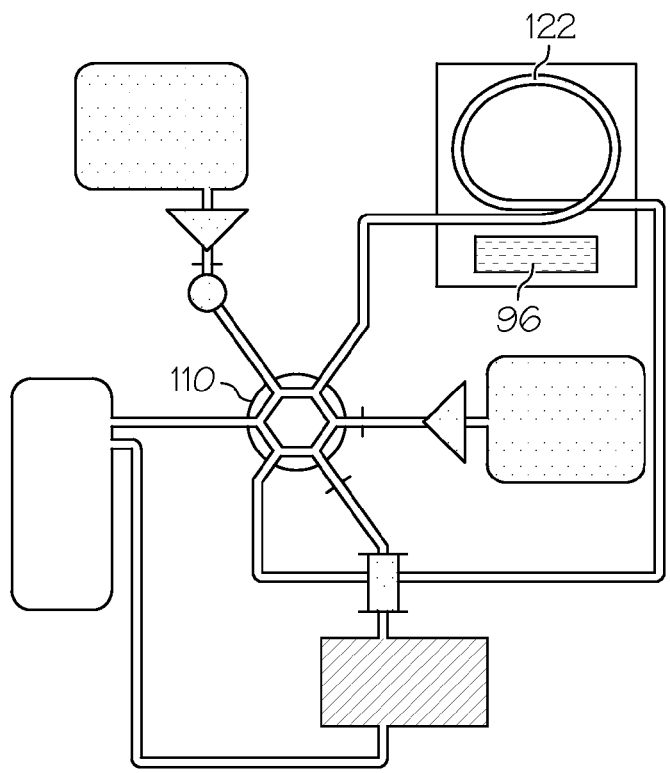
Figure 6C:
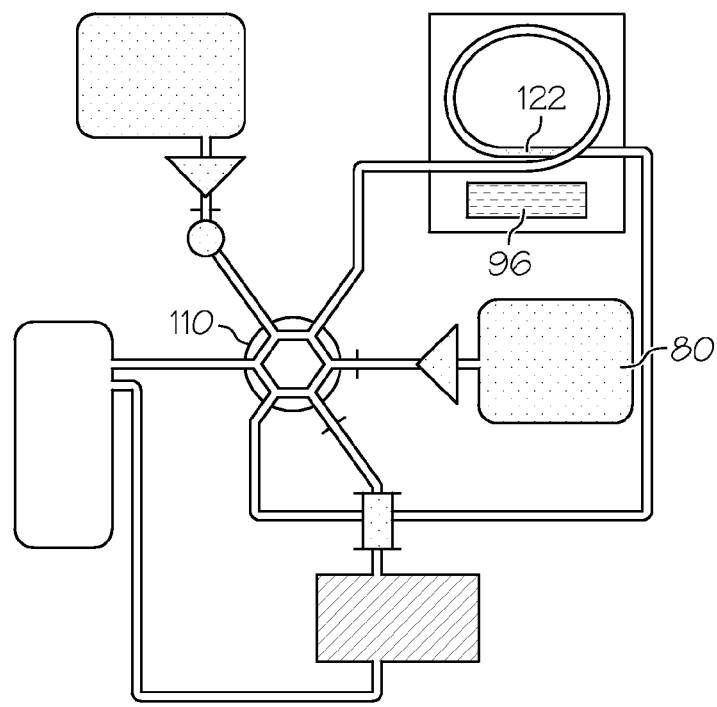
Figure 6D:
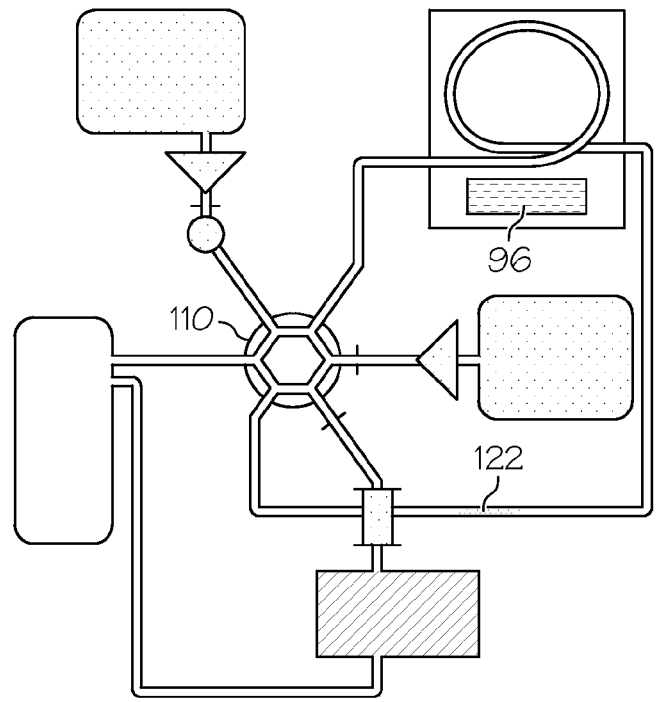

The construction of a particularly preferred device according to the invention is shown in FIG. 2. The device can be constructed to a large extent from commercial HPLC components. One component with a special function is the extractor (90). In a particularly preferred embodiment this is a toroidal core transformer which builds up a strong magnetic field when current flows and on which a HPLC line in the form of a loop is attached (FIG. 7). An HPLC line with an inner diameter between 0.2 mm and 2.0 mm is especially preferred. Preferred materials for the line are polyphenyl sulfone (PPSU), polyether ether ketone (PEEK) and silicone.

Another embodiment of the invention which is even more preferred is a device with a rotary extractor (FIG. 11). In Examples 4 and 5, the application of functionalized ferromagnetic micro-particles for the preparation of biological samples for quantitative chromatographic analysis of small molecules, with handling of these particles in a complex closed high pressure flow system with the rotary extractor is described. Sufficient and constant extraction recovery, and good clean-up efficacy was observed. Even without use of an internal standard compound, the principle enabled the implementation of a linear and reproducible method for the quantification of itraconazole as representative analyte with ultraviolet detection as a representative technique of detection in human plasma as a representative sample material.

In a preferred embodiment of the invention, manual injection of single samples can be used. If an autosampler with pipetting capability becomes integrated into such a system, the configuration described herein is suited to configure a compact front-end sample preparation and chromatography module for different detection techniques. Such an embodiment is even more preferred. In particular, development of a comprehensive LC-MS/MS analyzer including this sample introduction system is highly attractive.

Advantages of the working principle and the devices according to the invention over different so far used techniques of automatable extraction procedures prior to chromatographic analyses include: potentially very short cycle time; no solid consumables are required; no need for extensive robotic solutions; and potentially very compact footprint of a comprehensive sample clean-up and chromatography system.

In other aspects, the invention comprises the following further items as embodiments:

1. Device for the separation of magnetic or paramagnetic microparticles and the elution of an analyte adsorbed on said particles, the device being a liquid system (LS) comprising
    a first and a second inlet (10, 20) for a first and a second liquid mobile phase (65, 75),
    means for making fluidic connections (30),
    a means (switching unit) suitable for producing two different fluid connecting states (110),
    an extractor (90) with (i) an entry port (91), (ii) an exit port (92), (iii) a section (97) between said entry port and said exit port, the section comprising a fluid connecting line (95), and (iv) a means (96) capable of temporarily applying a local magnetic field to the fluid connecting line (95) in the section (97).

2. Device according to item 1, further comprising at least a pressure-generating means (40), an injection device (50), two storage containers (60, 70) for the first and the second mobile phase (65, 75), a collecting vessel (80), and an outlet (100), and further characterized in that
    the first inlet (10) is designed such that the first mobile phase (65) can be fed under pressure from the first storage container (60) to the LS via a fluidic connection;
    the first inlet (10) is additionally fluidically connected to an injection device (50), the injection device being designed such that it allows a mixture (120) of liquid sample material (121) and microparticles suspended therein (122) to be introduced into the first mobile phase that was introduced through the inlet;
    the second inlet (20) is designed such that the second mobile phase (75) can be fed under pressure from the second storage container (70) to the LS via a fluidic connection;
    the first inlet (10) is connected to a first entry port (E1) of the switching unit (110) and the second inlet (20) is fluidically connected to a second entry port (E2) of the switching unit;
    the entry port (91) of the extractor (90) is fluidically connected to a first exit port (A1) of the switching unit and the exit port (92) of the extractor (90) is fluidically connected to a third entry port (E3) of the switching unit;
    the second exit port (A2) of the switching unit (110) either is the outlet (100) or is fluidically connected to the outlet (100);
    the third exit port (A3) of the switching unit (110) is fluidically connected to the collecting vessel (80); and
    the switching unit (110) is suitable in a first connecting state (I) for fluidically connecting E1 and A1, E2 and A2 as well as E3 and A3 (also referred to as position (I)) and in the second connecting state (II) it is suitable for fluidically connecting E2 and A1, E3 and A2 as well as E1 and A3 (also referred to as position (II)).

3. Device according to item 2, characterized in that the LS is a high pressure LS (HLS), the HLS is preferably a substantially closed system and the outlet (100) is fluidically connected to a separation unit (130) and the separation unit is fluidically connected to a detector (140) and the exit port (145) of the detector is fluidically connected to the collecting vessel (80).

4. Device according to item 3, characterized in that the separation unit (130) is a chromatography column.

5. Device according to one of the items 3 or 4, characterized in that the detector (140) is selected from the group comprising UV/Vis spectrometer, diode array detector, light scatter detector, fluorescence detector, refractive index detector, mass spectrometer, conductivity detector, electrochemical detector.

6. Device according to any of the items 1 to 5, characterized in that the switching unit (110) is a rotary valve switching unit suitable for producing two different fluid connecting states.

7. Device according to any of the items 1 to 6, characterized in that in the extractor (90) the means (96) capable of temporarily applying a local magnetic field to the fluid line (95) in the section (97) comprises a controllable electromagnet.

8. Device according to item 7, characterized in that the line (95) in the extractor comprises two or more consecutive sections, and the local magnetic field is applied to the two or more consecutive sections.

9. Device according to item 8, characterized in that the line (95) in the extractor comprises two consecutive sections (97a, 97b), and the local magnetic field is applied to the two consecutive sections (97a, 97b) of this line.

10. Device according to any of the items 8 or 9, characterized in that the connecting line (95) between the entry port (91) and exit port (92) of the extractor (90) is a helix with one or more windings (99), also referred to as a loop(s), where each of the sections to which the local magnetic field is applied are arranged side by side.

11. Device according to item 9, characterized in that the line (95) between the entry port (91) and exit port (92) of the extractor (90) is designed as a helix with one winding (99), also referred to as a loop, where each of the sections (97a, 97b) of the line leading to the entry port and exit port are arranged side by side.

12. Device according to item 11 and FIG. 3B, characterized in that the line (95) between the entry port (91) and exit port (92) of the extractor (90) has a helical design and has two or more windings or loops (99a, 99b) where one or more sections (97c) of the windings and each of the sections (97a, 97b) of the line leading to the entry port (91) and exit port (92) are arranged side by side.

13. Device according to one of the items 7 to 12, characterized in that the electromagnet is arranged such that the magnetic field can act on two or more sections (97) of the line (95) arranged side by side between the entry port (91) and exit port (92) of the extractor (90).

14. Device according to one of the items 7 to 13, additionally comprising a control unit and characterized in that the control unit controls the electromagnet.

15. Device according to one of the items 1 to 6, characterized in that
    the means (96) comprises a rotatable circular disk (200) with a controllable actuator (220) capable of adjusting the disk, by way of rotation, in a first and a second position;

a fraction of the circumference of the disk (200) is located in proximity to the fluid connecting line (95) of the section (97);

one or more permanent magnets (210) are attached on the disk, in the first position of the disk the magnetic field of the one or more magnets is applied to the fluid connecting line (95) of the section (97); and in the second position of the disk the magnetic field applied to the fluid connecting line (95) of the section (97) is reduced.

16. Device according to item 15, characterized in that the fraction of the circumference of the disk (200) which is located in proximity to the fluid connecting line (95) of the section (97) is a contiguous part of the circumference and comprises up to about one half of the circumference of the disk (200).

17. Device according to one of the items 15 and 16, characterized in that the section (97) of the fluid connecting line (95) in the extractor (90) is arranged in parallel to a fraction of the circumference of the edge of the rotatable circular disk (200).

18. Device according to one of the items 16 and 17, characterized in that the fraction comprises at least 1% of the circumference of the disk (200); preferably the fraction is between about 5% and about 50%, more preferred between about 20% and about 50%, even more preferred between 40% and 50%, of the circumference of the disk (200), even more preferred the fraction has a value selected from the group consisting of about 25%, about 30%, about 35%, about 40%, about 45%, and about 50%.

19. Device according to one of the items 15 to 18, characterized in that the one or more permanent magnets (210) are located on the edge of the disk (200).

20. Device according to any of the items 15 to 19, characterized in that the one or more magnets are localized on a segment of the disk (200).

21. Device according to any of the items 15 to 20, characterized in that a plurality of magnets is attached in or on the disk (200).

22. Device according to one of the items 1 to 21, additionally comprising a control unit and characterized in that the control unit controls the pressure-generating means (40), and the switching unit (110).

23. Device according to one of the items 1 to 22, characterized in that the pressure-generating means comprises two HPLC pumps.

24. Device according to one of the items 1 to 23, characterized in that the collecting vessel (80) comprises a magnet or electromagnet.

25. Device according to one of the items 1 to 24, additionally comprising a first (65) and a second (75) mobile phase in a liquid state of aggregation.

26. Device according to one of the items 1 to 25, additionally comprising magnetic or paramagnetic microparticles (122).

27. Device according to item 26, characterized in that the microparticles have a functionalized surface (123).

28. Device according to item 27, characterized in that the surface allows the adsorption of an analyte.

29. Device according to item 28, characterized in that the surface of the microparticles is hydrophobic.

30. Device according to item 28, characterized in that the surface of the microparticles is hydrophilic.

31. Device according to item 28, characterized in that the surface is selected from the group comprising anion exchange material, cation exchange material, mixed hydrophobic and hydrophilic copolymers and silica.

32. Device according to item 29, characterized in that the surface comprises C1-C50, preferably C5-C20 hydrocarbon residues.

33. Device according to one of the items 26 to 32 additionally comprising a liquid sample material.

34. Device according to item 33, characterized in that the sample material is a suspension.

35. Device according to item 34, characterized in that the sample material is a homogenate.

36. Device according to one of the items 33 to 35, characterized in that the sample material contains food components, components of a soil sample or waste water.

37. Device according to item 33, characterized in that the sample material comprises a biological liquid, a suspension or a homogenate containing biological material or a lysate of biological material.

38. Device according to item 37, characterized in that the sample material is selected from the group comprising whole blood, citrate blood, heparin blood, EDTA blood, plasma, serum, urine, sputum, synovial liquid, bronchial lavage, respiratory air condensate and liquor.

39. Use of a device according to one of the items 1 to 38 for manipulating magnetic microparticles and two different mobile phases in a liquid state of aggregation.

40. Use according to item 39 additionally for manipulating liquid sample material.

41. Method for obtaining a purified analyte from a complex liquid sample material containing the said analyte comprising the steps (a) contacting the liquid sample material (121) containing the analyte with microparticles (122) made of a magnetic or paramagnetic material with a functionalized surface (123) whereby the analyte (124) adsorbs to the surface; followed by (b) introducing the sample material with the microparticles into a device according to one of the items 2 to 38 using the injection device (50); followed by (c) pumping a first mobile phase (65) from a first storage vessel (60) into the first inlet (10) of the device where the switching unit (110) of the device makes the connecting state (I) and in the extractor (90) a magnetic field is applied to the connecting line (95) within the section (97), the magnetic field being suitable for immobilizing the magnetic or paramagnetic microparticles (122) contained in the mobile phase entering through the line (95) on the nearest inner wall (93) of the line (95) facing the magnetic field in the first section (97); followed by (d) immobilizing the microparticles (122) in the extractor (90) on the inner wall (93) of the line (95) within the section (97) of the line; followed by (e) separating the microparticles (122) from the remaining sample material by further pumping the first mobile phase (65) from the first storage vessel (60) into the first inlet (10) whereby the immobilized microparticles are washed with the first mobile phase and the remaining sample material is fed into the collecting container (80); followed by (f) switching over the switching unit (110) into the connecting state (II) and pumping a second mobile phase (75) from the second storage vessel (70) into the second inlet (20) of the device where the second mobile phase (75) is suitable for detaching the adsorbed analyte from the surface of the microparticles (122); followed by (g) eluting the analyte by contacting the microparticles (122) with the second mobile phase (75); followed by (h) moving the second mobile phase containing the eluted analyte to the outlet (100) of the device by further pumping the second mobile phase (75) from the second storage vessel (70) into the second entry port (20) by means of which the analyte is obtained in a purified form at the outlet (100).

42. Method according to item 41, characterized in that the first mobile phase is water or an aqueous solution.

43. Method according to one of the items 41 and 42, characterized in that the second mobile phase is an organic solvent.

44. Method according to one of the items 41 to 43, characterized in that the second mobile phase is a nonpolar organic solvent.

45. Method according to one of the items 41 to 44, characterized in that the second mobile phase is a polar organic solvent.

46. Method according to one of the items 41 to 43, characterized in that the second mobile phase is an organic solvent which is selected from the group comprising a C1-C6 aliphatic alcohol, acetonitrile, methyl-tert-butyl ether (MTBE), acetone, ethyl acetate, hexane, dimethyl sulfoxide, diisopropyl ether, dichloromethane, trichloromethane and tetrachloromethane.

47. Method according to one of the items 41 to 46, characterized in that the sample material is a biological fluid, a suspension or a homogenate containing biological material or a lysate of biological material.

48. Method according to item 47, characterized in the sample material is selected from the group comprising whole blood, citrate blood, heparin blood, EDTA blood, plasma, serum, urine, sputum, synovial fluid, bronchial lavage, respiratory air condensate and liquor.

49. Method for detecting an analyte in a complex liquid sample material containing said analyte, comprising the steps
   (a) providing a device according to one of the items 2 to 38;
   (b) obtaining the purified analyte from the sample material using a method according to one of the items 41 to 48, wherein the analyte is obtained in a purified form at the outlet (100) of the device and the switching unit (110) makes the connecting state (II);
   (c) moving the second mobile phase containing (i) the analyte and (ii) optionally further substances that were eluted from the microparticles together with the analyte through the separation unit (130) and into the detector (140) where the movement is driven by pumping the second mobile phase (75) from the second storage vessel (70) into the second entry port (20);
   (d) detecting the analyte by the detector (140).

50. Method according to item 49, characterized in that step (d) is followed by the steps
   (e) switching over the switching unit (110) into the connecting state (II);
   (f) weakening or removing the magnetic field in the extractor (90);
   (g) pumping the first mobile phase (65) from the second storage vessel (60) into the first inlet (10) during which the microparticles (122) are moved towards the collecting vessel (80);
   (h) moving the microparticles with the first mobile phase into the collecting vessel.

The following examples, publications and figures further elucidate the invention the protective scope of which is derived from the patent claims. The described devices and processes are to be understood as examples which still describe the subject matter of the invention even after modifications.

SPECIFIC EMBODIMENTS

Example 1

Description of the Use of the Device According to the Invention

In general the device can be designed to be used cyclically where the stages of a cycle can be subdivided as an example into A-D. In this connection reference is made to FIGS. 1-7 and in particular to FIG. 6 A-D.

A—After the mixture of sample material and extraction particles has been injected, the mixture reaches the extractor where the particles (122) are immobilized for the first time. This stage corresponds to the situation in the extractor shown in FIG. 5A. The switching unit is in position (I) as a result of which the first mobile phase is passed into the system. A magnetic field symbolized by the horizontal texture of (96) is applied by means of the means (96).

B—The switching unit is in position (II) as a result of which the second mobile phase is passed into the system. After separation of the remaining sample material from the particles and the change from the first to the second mobile phase, the extraction particles (122) reach the loop of the extractor corresponding to the situation shown in FIG. 5B. In this process step no magnetic field is applied or the magnetic field is reduced to such an extent that the extraction particles are again mobile symbolized by the perpendicular texture of (96). The holding time of the extraction particles in the loop (99) is preferably adjusted such that at least 20%, more preferably at least 30%, even more preferably at least 50% and even more preferably 75% and even more preferably at least 90% of the analyte is eluted into the second mobile phase. For quantitative determinations it is advantageous that the amount of the eluted analyte is proportional to the concentration of the analyte in the sample material for the same elution times.

C—In the subsequent step a magnetic field is again applied to the line in front of the exit port of the extractor (see texture of (96)). The particles (122) suspended in the mobile phase that flows past are again immobilized corresponding to the situation shown in FIG. 5C. The switching unit is also in position (II) in this process step as a result of which the substances (also including the analyte) detached from the particles together with the second mobile phase are conveyed to the separation unit and to the detector. The magnetic field generated by (96) is maintained during this and the particles (122) are retained.

D—After the separation and detection step is completed, the device is regenerated. The switching unit is brought into position (I) and the first mobile phase is passed into (pumped into) the liquid system. In this process step no magnetic field is applied or the magnetic field is reduced to such an extent that the extraction particles are again mobile, symbolized by the perpendicular texture of (96). The particles (122) are transported together with the liquid phase which surrounds them into the collecting vessel (80). The particles can be optionally concentrated in the container by a local magnetic field in order to for example make them more accessible to a recovery.

Example 2

Processing and Analysis of Sample Material

Serum as an example of a biological sample material is mixed with a suspension of C18-functionalized ferromagnetic microparticles (extraction particles). In the mixing process analyte molecules of low polarity are adsorbed to the hydrophobic chains of the microparticles. The mixture of sample and particles is injected via an injection valve into the device according to the invention. The first mobile phase of this system is an aqueous solution. The mixture of sample and particles is transferred to an electromagnet by passing in the first mobile phase. Here the ferromagnetic particles loaded with analyte are retained and immobilized in the tubing system with the aid of the activated electromagnet. The non-particle-bound sample matrix is transported by the continuous flow of the first mobile phase into the collecting vessel (waste). The aqueous mobile phase is then replaced in the tubing system by an organic solvent as the second mobile phase with the aid of a 6 port HPLC switching valve. The electromagnet is de-energized for a short period; the particles are resuspended in the organic solvent in the loop of the extractor and the target analyte is detached from the functionalized particles. After a few seconds the electromagnet is again switched on and the particles which have in the meantime become mobile in the tube loop are again immobilized. The target analyte molecules eluted from the particles are transferred directly onto an analytic chromatography column. A chromatographic detector is connected in series to this separation column. A prototype of an extraction system was constructed on the basis of this working principle and its extractor is shown in FIG. 7.

Example 3

Test Measurement Using the Device According to the Invention

The antimicrobial pharmacological agent itraconazole was examined as an example of an analyte of in-vitro diagnostics. This substance was quantified in a therapeutic concentration range from a human sample matrix. For this purpose serum samples containing known itraconazole concentrations determined by means of LC tandem mass spectrometry as well as "drug-free" sera were examined.

C18-modified magnetic or paramagnetic extraction particles from the Dynal Company (Oslo, Norway) were used (DYNABEADS 18, 50 mg/ml, Dynal, Inc.). 15 µl of this bead suspension was pipetted into a reaction vessel; this was positioned on a permanent magnetic particle extractor (Dynal MPC-S Magnetic Particle Concentrator). The particle-free solvent medium was removed. The particles were then washed twice with 200 µl 0.1% trichloroacetic acid in each case; for this purpose the reaction vessel was repeatedly removed from the extractor and again positioned therein in order to immobilize the particles. Finally the particles were suspended in 1000 µl water.

In order to analyse the serum samples using the system described in the present invention, 15 µl sample was mixed with 15 µl of the prepared aqueous particle suspension in a reaction vessel. This mixture was in each case injected into the described device by a manual injection valve and processed according to the work process described above. The aspiration of sample aliquots, the mixing of sample and extraction particles and the injection which are carried out manually in a first prototype setup can also be carried out fully automatically using a conventional autosampler.

FIGS. 8 A-C show examples of chromatograms of the analysis of a blank sample (a), a calibrator sample (b) containing an itraconazole concentration of 2.9 mg/l as well as a pooled patient sample (c). When the patient sample is quantified on the basis of the calibrator sample, a concentration of 2.0 mg/l is calculated. The same result was found for this sample using a recognized mass spectrometric analytical method for determining itraconazole (Vogeser M, Spohrer U, Schiel X. Determination of itraconazole and hydroxyitraconazole in plasma by use of liquid chromatography-tandem mass spectrometry with on-line solid-phase extraction. Clin. Chem. Lab. Med. 2003; 41:915-20).

Example 4

Extractor with Rotary Disk

The principle was again to inject sample materials together with functionalized ferromagnetic micro-particles into a HPLC system. The particles were immobilized reversibly onto the inner surface of HPLC tubes by a magnet. Different mobile phases pumped through this HPLC tube were exchanged rapidly by use of two HPLC pumps interacting via a high pressure switching valve. By these means, the particles underwent the extractive steps of adsorption, washing, and elution within very short time intervals, and within a closed system. Extracts were eluted to different detectors.

Based on this principle, we configured a chromatographic system of two isocratic HPLC pumps, a manual injector, a high-pressure switching valve, an analytical HPLC column, an UV-detector with chromato-integrator, and furthermore a rotary extractor device. The components were connected with HPLC tubings as shown in FIG. 11 and FIGS. 12-16. The rotary extractor used is shown in FIG. 17. The HPLC pump 1 in element (230) and the HPLC pump 2 in element (240) each were a Waters 600 pump with a programmable controller, which also controlled the switching valve (110) and the rotary extractor.

In the particularly useful rotary extractor device (FIG. 17), several cubic magnets were fixed on a plastic disk of approx. 15 cm diameter. The disk was rotated by an electric servo drive by 180°, thus alternating between a first and a second position. A transparent HPLC tube (inner diameter 0.75 mm) was fixed close around the disk semicircularly. The orientation of the magnet bearing disk and the HPLC tube was such that in the first position (see FIG. 10 A, FIGS. 12-15)) the magnets were close to the tube (immobilisation of beads from the flow), while in the second position (FIG. 10 B, FIG. 16) the magnets were distant from the tube (re-mobilisation of beads into the flow).

Commercially available ferromagnetic microparticles with C18 modified surface were used (DYNABEADS RPC18 (Prod. No. 102.01), Invitrogen, Karlsruhe, Germany; 12.5 mg/mL, mean particle diameter 1 µm). After conditioning of the particles according to the manufacturer's instruction with trichloroacetic acid, a 2.5 mg/ml suspension of the beads in distilled water was prepared.

For sample, extraction 40 µl of sample and of the bead suspension were aspirated into a 50 µL glass-syringe. This mixture was injected into the flow of HPLC pump 1. The manual injection valve gave a starting signal to the chromato-integrator and to the pump controller. Pump 1 continuously delivered methanol/water (10/90) with a flow of 2 ml/min throughout the entire process (FIGS. 12, 13). Via a high pressure switching valve the injected sample mixture was transferred to the extractor device. Analyte adsorption to the functionalized bead surface took place beginning in the injection syringe and continuing after injection within the tubings. The extractor device in the first position retained the analyte charged particles (122 with 124) on the inner surface of the HPLC tube, while the sample matrix was washed by the continuous flow of the mobile phase from pump 1 to waste (FIG. 14). After one minute of washing, the high pressure switching valve (SW) (110) was switched into the second position by the pump controlling program (15). Now, HPLC pump 2 delivered 70% acetonitrile/30% 0.1% formic acid to the extractor device. The high content of organic solvent eluted the analyte from the immobilized beads. The extract was transferred from the extractor onto the analytical column (130) and was submitted to analytical chromatography with subsequent UV detection and data recording. After one minute of elution, the switching valve was again set to the first position; simultaneously, the extractor was switched to the second position, leading to the re-mobilisation of the beads into the flow (FIG. 16). The beads were thus purged into waste for one minute until the end of the sample preparation cycle after three minutes. Efficient immobilisation and re-mobilisation of the particles within the transparent tubing was observed visually.

Example 5

Analysis of Samples from Patients

The function of the system described in Example 4 was shown by quantifying the concentrations of the antimycotic drug itraconazole as a representative compound in patients' plasma samples. Specific conditions were as follows: Analytical column, LiChrosphere 100 70×3 mm, C18, 5 µM, Fa. Maisch, Ammerbuch, Germany; flow HPLC pump 1: 2.0 ml/min (10% methanol/90% water); flow HPLC pump 2: 1.2 ml/min (70% acetonitrile/30% 0.1% formic acid); injection loop volume 100 µl; injected volume 50 µl (mixture of sample and bead suspension); UV detection at 263 nm; retention time of itraconazole was approximately 4.9 min.

To test the linearity and reproducibility of the analytical system, a calibration series of itraconazole spiked plasma samples (125 µg/l, 250 µg/l, 500 µg/l, 1,000 µg/l, and 2,000 µg/l) was analyzed; and samples from a patients' plasma pool were analyzed in eight replicates. A linear calibration function was observed ($r^2$>0.99); in the pool samples a mean concentration of 378 µg/l was found, with a coefficient of variation of 7.9%. Representative chromatograms from a plasma blank and from a pool sample are shown in FIG. 18A, B.

To test the recovery of the extraction process, an isocratic pump was directly connected to the injector, the analytical column, and the detector. A pure solution of itraconazole in 10% methanol (3,000 µg/l) was injected in duplicate and the peak area was recorded. The same solution was then injected in duplicate to the described extraction configuration using ferromagnetic micro-particles. Mean peak areas were compared, and an extraction recovery of 72% was found.

What is claimed is:

1. A liquid system (LS) device comprising
a first and a second inlet for a first and a second liquid mobile phase,
a means for producing two different fluid connecting states, and
an extractor having (i) an entry port, (ii) an exit port, (iii) a section between said entry port and said exit port, the section comprising a fluid connecting line, and (iv) a means for temporarily applying a local magnetic field to the fluid connecting line in the section, wherein the first inlet, the second inlet and the extractor are each fluidly connected to the means for producing two different fluid connecting states,
the means for temporarily applying a local magnetic field to the fluid connecting line in the section comprises a rotatable circular disk with a controllable actuator for adjusting the disk, by way of rotation, in a first and a second position;
a fraction of the circumference of the disk is located in proximity to the fluid connecting line of the section;
in a segment of the disk, one or more permanent magnets are attached;
in a first position of the disk, the magnetic field of the one or more magnets is applied to the fluid connecting line of the section; and
in a second position, the magnetic field applied to the fluid connecting line of the section is reduced.

2. The device according to claim 1 further comprising at least a pressure-generating means, an injection device, first and second storage containers for the first and the second mobile phase, a collecting vessel, and an outlet, and further wherein
the first inlet is designed such that the first mobile phase can be fed under pressure from the first storage container to the means for producing two different fluid connecting states via a fluidic connection;
the first inlet is additionally fluidically connected to the injection device, the injection device being designed to allow a mixture of liquid sample material and microparticles suspended therein to be introduced into the first mobile phase introduced through the first inlet;
the second inlet is designed such that the second mobile phase can be fed under pressure from the second storage container to the means for producing two different fluid connecting states via a fluidic connection;
the first inlet is connected to a first entry port (E1) of the means for producing two different fluid connecting states and the second inlet is fluidically connected to a second entry port (E2) of the means for producing two different fluid connecting states;
the entry port of the extractor is fluidically connected to a first exit port (A1) of the means for producing two different fluid connecting states and the exit port of the extractor is fluidically connected to a third entry port (E3) of the means for producing two different fluid connecting states;
the second exit port (A2) of the means for producing two different fluid connecting states is the outlet or is fluidically connected to the outlet;
a third exit port (A3) of the means for producing two different fluid connecting states is fluidically connected to the collecting vessel; and
the means for producing two different fluid connecting states is suitable in a first connecting state (I) for fluidically connecting E1 and A1, E2 and A2 as well as E3 and A3 and in a second connecting state (II) is suitable for fluidically connecting E2 and A1, E3 and A2, as well as E1 and A3.

3. The device according to claim 2 wherein the LS is a high pressure LS (HLS), the HLS is a closed system and the outlet is fluidically connected to a separation unit and the separation unit is fluidically connected to a detector and the exit port of the detector is fluidically connected to the collecting vessel.

4. The device according to claim 1 wherein the section of the fluid connecting line in the extractor is arranged in parallel to about half of the circumference of the edge of the rotatable circular disk.

5. The device according to claim 4 wherein the one or more permanent magnets are located on the edge of the disk.

6. The device according to claim 5 wherein a plurality of magnets are localized in the segment.

7. The device according to claim 1 wherein the disk additionally comprises a controllable actuator capable of effecting rotational movement of the disk.

8. The device according to claim 1 wherein the LS is a high pressure LS (HLS).

9. The device according to claim 1 wherein the HLS is a substantially closed system and the outlet is fluidically connected to a separation unit and the separation unit is fluidically connected to a detector and the exit port of the detector is fluidically connected to the collecting vessel.

10. The device according to claim 1 additionally comprising a first and a second mobile phase in a liquid state of aggregation.

11. The device according to claim 1 additionally comprising magnetic or paramagnetic microparticles.

12. The device according to claim 11 additionally comprising a liquid sample material.

13. A method for obtaining a purified analyte from a complex liquid sample material containing the analyte, the method comprising the steps of:
  contacting the liquid sample material with microparticles comprising a magnetic or paramagnetic material with a functionalized surface whereby the analyte adsorbs to the surface;
  introducing the sample material with the microparticles into the device according to claim 2 via the injection device
  introducing the sample material with the microparticles into a device according to claim 3 using an injection device;
  pumping a first mobile phase from a first storage vessel into the first inlet of the device where the switching unit of the device makes the connecting state (I) and in the extractor a magnetic field is applied to the connecting line within the section, the magnetic field being suitable for immobilizing the magnetic or paramagnetic microparticles contained in the mobile phase entering through the line on the nearest inner wall of the line facing the magnetic field in the first section;
  immobilizing the microparticles in the extractor on the inner wall of the line within the section of the line;
  separating the microparticles from the remaining sample material by further pumping the first mobile phase from the first storage vessel into the first inlet whereby the mobilized microparticles are washed with the first mobile phase and the remaining sample material is fed into the collecting container;
  switching over the switching unit into the connecting state (II) and pumping a second mobile phase from the second storage vessel into the second inlet of the device where the second mobile phase is suitable for detaching the adsorbed analyte from the surface of the microparticles;
  eluting the analyte by contacting the microparticles with the second mobile phase; and
  moving the second mobile phase containing the eluted analyte to the outlet of the device by further pumping the second mobile phase from the second storage vessel into the second entry port whereby the analyte is obtained in a purified form at the outlet.

* * * * *

UNITED STATES PATENT AND TRADEMARK OFFICE
CERTIFICATE OF CORRECTION

PATENT NO. : 8,337,705 B2  
APPLICATION NO. : 12/464153  
DATED : December 25, 2012  
INVENTOR(S) : Michael Vogeser Page 1 of 1

It is certified that error appears in the above-identified patent and that said Letters Patent is hereby corrected as shown below:

In the Claims

Col. 21, Line 26, "claim 2" should read --claim 3--.

Signed and Sealed this  
Eighth Day of July, 2014

Michelle K. Lee  
*Deputy Director of the United States Patent and Trademark Office*